US008647850B2

(12) United States Patent
Hitz et al.

(10) Patent No.: US 8,647,850 B2
(45) Date of Patent: Feb. 11, 2014

(54) PROCESS FOR SIMULTANEOUS SACCHARIFICATION AND FERMENTATION FOR PRODUCTION OF ETHANOL

(75) Inventors: William D. Hitz, Wilmington, DE (US);
Tom Huang, Fremont, CA (US);
Amanda Kathleen Iverson, Wilmington, DE (US); Brian G. Lefebvre, Wilmington, DE (US); Colin Mitchinson, Half Moon Bay, CA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 349 days.

(21) Appl. No.: 12/970,992

(22) Filed: Dec. 17, 2010

(65) Prior Publication Data

US 2011/0318803 A1   Dec. 29, 2011

Related U.S. Application Data

(60) Provisional application No. 61/289,749, filed on Dec. 23, 2009.

(51) Int. Cl.
*C12P 7/06*   (2006.01)

(52) U.S. Cl.
USPC ............................................. 435/161

(58) Field of Classification Search
USPC ................................................ 435/161, 183
See application file for complete search history.

(56) References Cited

U.S. PATENT DOCUMENTS

| | | | |
|---|---|---|---|
| 5,514,583 A | 5/1996 | Picataggio et al. | |
| 5,712,133 A | 1/1998 | Picataggio et al. | |
| 6,566,107 B1 | 5/2003 | Zhang | |
| 7,781,191 B2 | 8/2010 | Dunson, Jr. et al. | |
| 7,998,713 B2 * | 8/2011 | Dunson et al. | 435/161 |
| 2007/0031953 A1 * | 2/2007 | Dunson et al. | 435/161 |
| 2009/0203099 A1 | 8/2009 | Caimi et al. | |
| 2009/0246846 A1 | 10/2009 | Viitanen et al. | |
| 2009/0246876 A1 | 10/2009 | Viitanen et al. | |
| 2011/0014670 A1 | 1/2011 | Caimi et al. | |

FOREIGN PATENT DOCUMENTS

JP   2010246422 A   11/2010

OTHER PUBLICATIONS

Lau, Ming W. et al., Comparing the fermentation performance of *Escherichia coli* KO11, *Saccharomyces cerevisiae* 424(LNHST) and *Zymomonas mobilis* AX101 for cellulosic ethanol production, Biotechnology for Biofuels, 2010, pp. 1-10, vol. 3, No. 11.
Um, Byung-Hwan et al., High-Solid Enzymatic Hydrolysis and Fermentation of Solka Floc into Ethanol, Journal of Microbiology and Biotechnology, 2008, pp. 1257-1265, vol. 18, No. 7.
Zhang, Mingjia et al., Ethanol production from high dry matter corncob using fed-batch simultaneous saccharifiation and fermentation after combined pretreatment, Bioresource Technology, 2010, pp. 4959-4964, vol. 101.
Dasari, Rajesh K. et al., The Effect of Particle Size on Hydrolysis Reaction Rates and Rheological Properties in Cellulosic Slurries, Applied Biochemistry and Biotechnology, 2007, pp. 289-299, vol. 136-140.
International Search Report dated Sep. 13, 2011, International Application No. PCT/US2010/061692.
Eklund, Robert et al., Simultaneous saccharification and fermentation of steam-pretreated willow, Enzyme and Microbial Technology, 1995, pp. 255-259, vol. 17, Elsevier Science Inc.
Feldmann, Sigrun D. et al., Pentose metabolism in *Zymomonas mobilis* wild-type and recombinant strains, Applied Microbiology and Biotechnology, 1992, pp. 354-361, vol. 38, Springer-Verlag.
Golias, Helen et al., Evaluation of a recombinant *Klebsiella oxytoca* strain for ethanol production from cellulose by simultaneous saccharification and fermentation: comparison with native cellobiose-utilising yeast strains and performance in co-culture with thermotolerant yeast and *Zymomonas mobilis*, Journal of Biotechnology, 2002, pp. 155-168, vol. 96, Elsevier Science B.V.
Lynd, Lee R. et al., Microbial Cellulose Utilization: Fundamentals and Biotechnology, Microbiology and Molecular Biology Reviews, Sep. 2002, pp. 506-577, vol. 66. No. 3, American Society for Microbiology.

* cited by examiner

*Primary Examiner* — Tekchand Saidha

(57) ABSTRACT

Methods are disclosed for the production of high concentrations of ethanol from biomass using *Zymomonas* as the ethanologen. *Zymomonas* is grown under conditions of low impeller agitation with high concentration of insoluble solids in a saccharification-fermentation mixture during a simultaneous saccharification and fermentation reaction for the production of high concentrations of ethanol.

18 Claims, 12 Drawing Sheets

PROCESS FOR SIMULTANEOUS SACCHARIFICATION AND FERMENTATION FOR PRODUCTION OF ETHANOL

This application claims the benefit of U.S. Provisional Patent Application, 61/289749, filed Dec. 23, 2009.

FIELD OF THE INVENTION

The invention relates to methods for the generation of ethanol from cellulosic biomass. Specifically, *Zymomonas* is used under specific simultaneous saccharification and fermentation process conditions for the production of high concentrations of ethanol.

BACKGROUND OF THE INVENTION

Fuel ethanol produced from renewable resources is one of the long-term solutions to global fossil fuel shortages, rising energy costs, and global warming effects related to increased atmospheric carbon dioxide. Fuel ethanol from renewable resources is produced by fermentation of sugars. Currently in the United States, glucose derived from corn grain is the most abundant sugar source for ethanol production. Due to the demands for corn grain as a feed and food supply, methods of converting various types of cellulosic biomass (including hemicellulose) to fermentable sugars are being developed. Sugar derived from this biomass source is a mixture of hexoses and pentoses, primarily glucose and xylose. As a result of developments in cellulosic biomass processing, these sugars may be released in high concentrations and used in fermentation in high concentrations to produce ethanol, with reduced water consumption and higher throughput. As such, conversion of biomass to ethanol poses great possibility for improving environmental impacts by providing a potentially economically viable alternative to fossil fuels.

Typical processes for the conversion of cellulosic biomass to ethanol comprise three steps; chemical and/or physical treatment of the biomass to reduce the lignin content of the biomass and to make polysaccharides available for enzymatic hydrolysis; saccharification or digestion or hydrolysis where polysaccharides are enzymatically converted to fermentable sugars; and fermentation where the fermentable sugars are consumed by an ethanologen for the production of ethanol. In some cases, depending on the conditions and the nature of the ethanologen, it may be energetically most efficient to combine the saccharification and fermentation steps. Optimization of each of these steps is needed for the production of high concentrations of ethanol.

Ethanologens have typically been yeast (e.g. *Saccharomyces*) or bacteria (e.g. *Zymomonas*). *Zymomonas* is well suited for the production of ethanol as it is generally robust, grows in relatively high glucose concentrations, and can be engineered to utilize C5 sugars such as xylose and arabinose (common products of saccharification) for ethanol generation. However, effective utilization of *Zymomonas* requires improving processes for using *Zymomonas* as an ethanologen.

The use of *Zymomonas* as an ethanologen is known (Sadler et al., Can. J. Microbiol. (1982), 28(12), 1311-19: Golias et al., J. Biotechnol., (26 Jun. 2002) (96) 2, pp. 155168; Ma et al., Renewable Energy (2009) 34:1466-1470), however *Zymomonas* is sensitive to high concentrations of acetate produced by many of the biomass pretreatment methods. Reduction of acetate levels can be achieved by methods such as washing pretreated biomass (Teixeira et al., Appl. Biochem. Biotechnol., (Spring, 2000) Vol. 84-86, pp. 111-127).

The use of a xylose utilizing *Zymomonas* in simultaneous saccharifcation and fermentation is also known, where the biomass was treated with sodium hydroxide followed by peracetic acid and washed (Teixeira et al. Supra). Eklund et al. (Enzyme and Microbial Technology (1995), 17(3), 255-9) demonstrated simultaneous saccharification and fermentation using *Zymomonas* as the ethanologen where the biomass was pre-treated with steam and sulfur dioxide and washed, then fermentation was at a total insoluble solids concentration of about 10% in both flasks and fermenters with some agitation, where the production of ethanol was about 28 g/L.

Additionally McMillan et al., (Appl. Biochem. Biotechnol. (1999) Vol. 77-79:649-665.) demonstrated the use of *Zymomonas* in a simultaneous saccharification and fermentation process where the strain of *Zymomonas* was adapted to poplar hydrolysate, the biomass was pre-treated with dilute acid then MTBE extracted, the saccharification enzyme was cellulase, and where the fermentation was run in a fermenter with 11.5% insoluble solids and an agitator at 150 RPM. Using this method the authors were able to achieve production of about 35 g/L ethanol.

The above methods demonstrate that *Zymomonas* may be used in processes of simultaneous saccharification and fermentation for the production of ethanol. However, the production of ethanol using these methods is low and it is clear that the processes need to be optimized to effect the production of ethanol in commercial quantities.

SUMMARY OF THE INVENTION

The methods of the invention seek to solve the problem of optimizing the use of a prokaryotic ethanologen in simultaneous saccharification and fermentation (SSF) processes via identifying conditions that allow for the use of high input insoluble solids content in the saccharification and fermentation mixture, and that support production by the prokaryotic ethanologen such that high ethanol production is achieved. Ethanol production using the present methods may be in excess of 60 g/L.

Accordingly the invention provides a method for the production of ethanol comprising:

a) providing pretreated biomass comprising insoluble solids and polysaccharides;

b) providing at least one saccharification enzyme for the conversion of polysaccharides to fermentable sugars;

c) providing a prokaryotic ethanologen;

d) preparing, in a bioreactor comprising an agitation means, a saccharification-fermentation mixture comprising the pretreated biomass of a), the saccharification enzyme of b), and the prokaryotic ethanologen of c); and e) growing the prokaryotic ethanologen in the saccharification-fermentation mixture wherein the concentration of total input insoluble solids in the saccharification-fermentation mixture is at least about 16% based on dry weight per liter, and wherein the prokaryotic ethanologen produces ethanol. In one aspect of the invention the agitation means of the invention provides no more power than about 0.2 watt/kg of total saccharification-fermentation mixture.

In another aspect the invention provides a method for the production of ethanol comprising:

a) providing pretreated biomass of particle size equal to or less than about 100 μm or a particle size of equal to or more than about 600 μm, comprising insoluble solids and polysaccharides;

b) providing at least one saccharification enzyme for the conversion of polysaccharides to fermentable sugars;

c) providing a prokaryotic ethanologen;

d) preparing in a bioreactor comprising an agitation means a saccharification-fermentation mixture comprising the pretreated biomass of a), the saccharification enzyme of b), and the prokaryotic ethanologen of c); and e) growing the prokaryotic ethanologen in the saccharification-fermentation mixture wherein:

1) the concentration of total input insoluble solids in the saccharification-fermentation mixture is at least about 16% based on dry weight per liter; and 2) wherein the prokaryotic ethanologen produces ethanol.

In another aspect the invention provides a saccharification-fermentation system comprising:

a) a pretreated biomass comprising insoluble solids and polysaccharides;

b) at least one saccharification enzyme for the conversion of polysaccharides to fermentable sugars; and c) a prokaryotic ethanologen;

wherein the biomass of (a), enzyme of (b), and ethanologen of (c) are combined in a saccharification-fermentation mixture, having a concentration of total input insoluble solids that is at least about 16 wt. % based on dry weight per liter.

BRIEF DESCRIPTION OF THE FIGURES, BIOLOGICAL DEPOSITS AND SEQUENCE DESCRIPTIONS

Applicants have made the following biological deposits under the terms of the Budapest Treaty on the International Recognition of the Deposit of Microorganisms for the Purposes of Patent Procedure:

Information on Deposited Strains

| Depositor Identification Reference | International Depository Designation | Date of Deposit |
|---|---|---|
| Zymomonas ZW658 | ATCC No PTA-7858 | Sep. 12, 2006 |

Figure 3A:
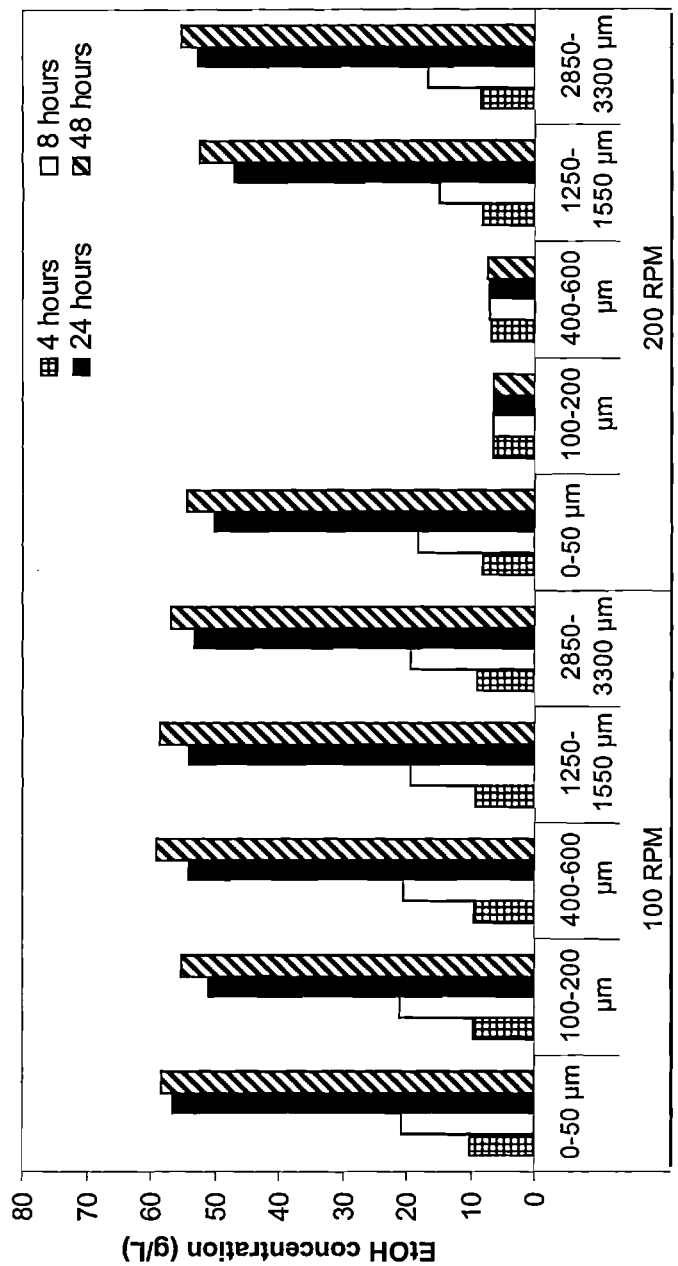

FIGS. 3A and B are graphs showing the effects of different particle sizes on fermentation using recombinant Zymomonas mobilis using Ballotini glass beads with varying particle size in a 25% solids loading. A and B are different experiments using different particle size ranges.

Figure 4:
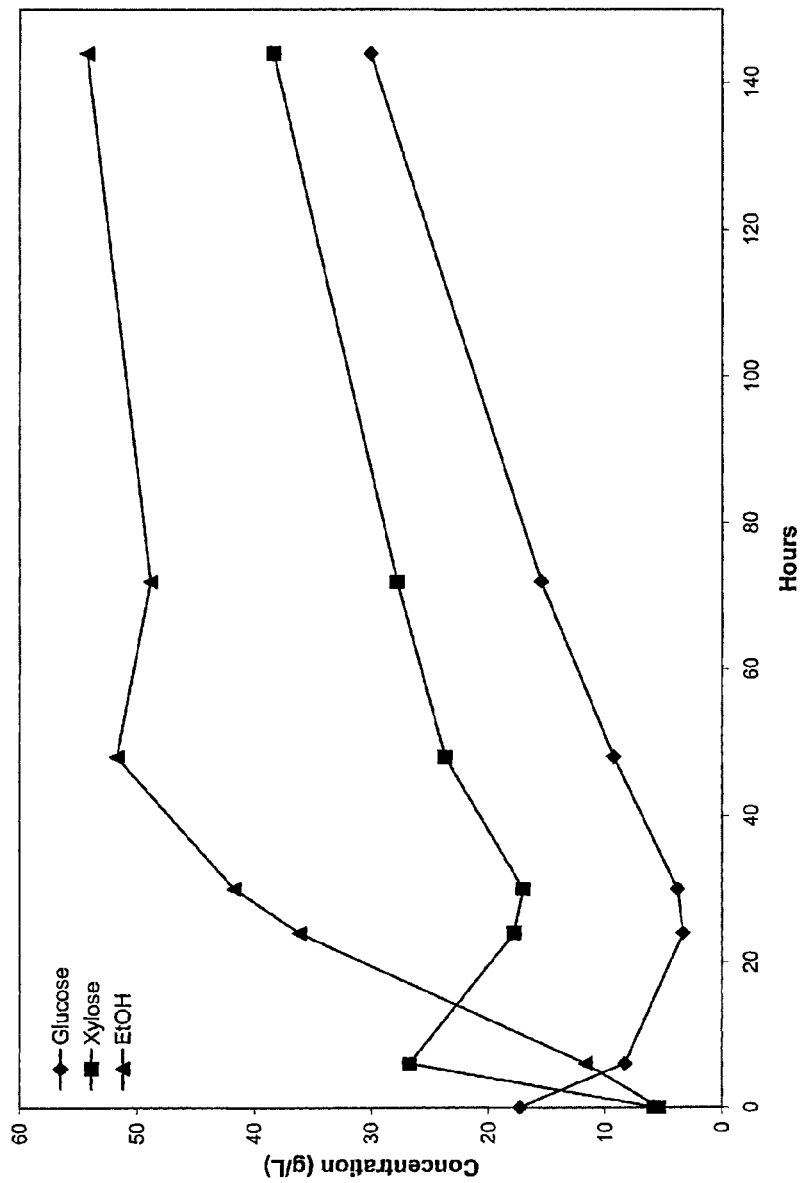

FIG. 4 is a graph showing ethanol, xylose and glucose concentrations from a 1L SSF scale-up with two Rushton 6-bladed impellers (45 mm diameter) revolving at 100 RPM.

Figure 5:
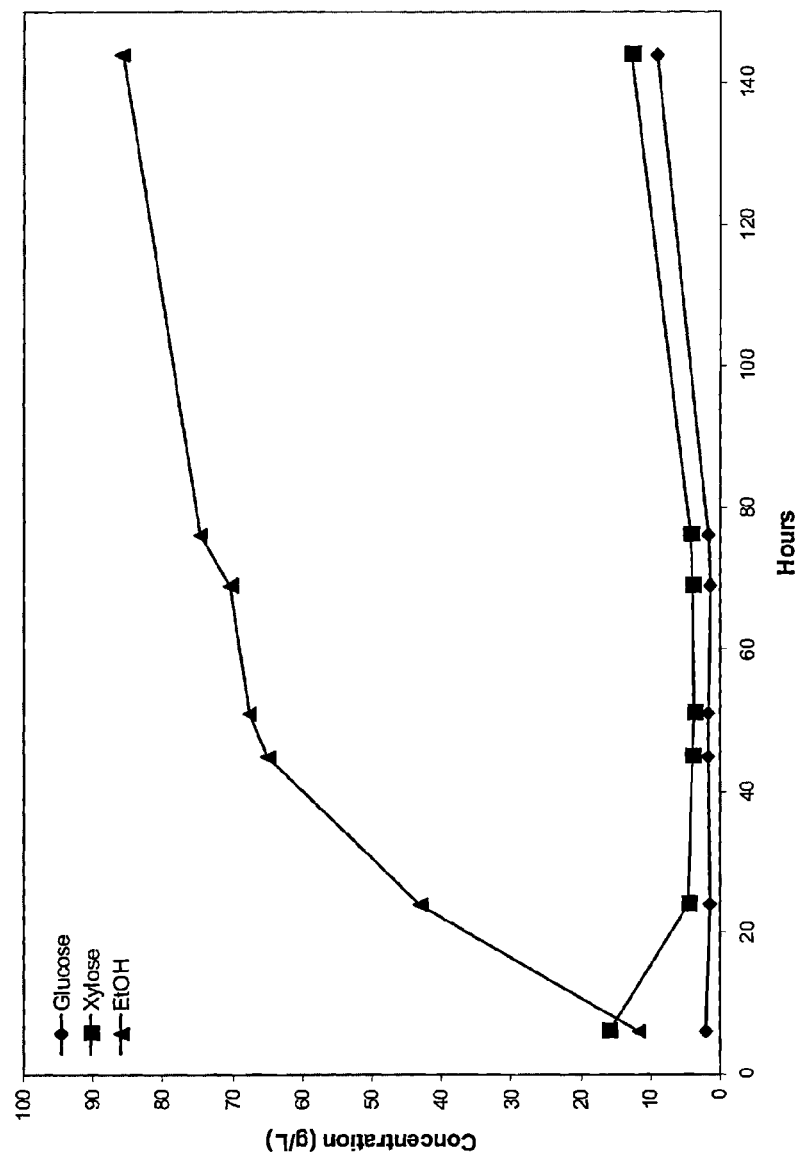

FIG. 5 is a graph showing ethanol, xylose and glucose concentrations from a 1 L SSF scale-up with two marine 6-bladed impellers (45 mm diameter) revolving at 150 RPM.

FIG. 6 is a graph showing ethanol production in SSF runs with initial 25 wt % biomass addition and stirring at 250 or 750 RPM (A); or with partitioned biomass addition and stirring at 80 or 250 RPM (B).

Figure 7A:
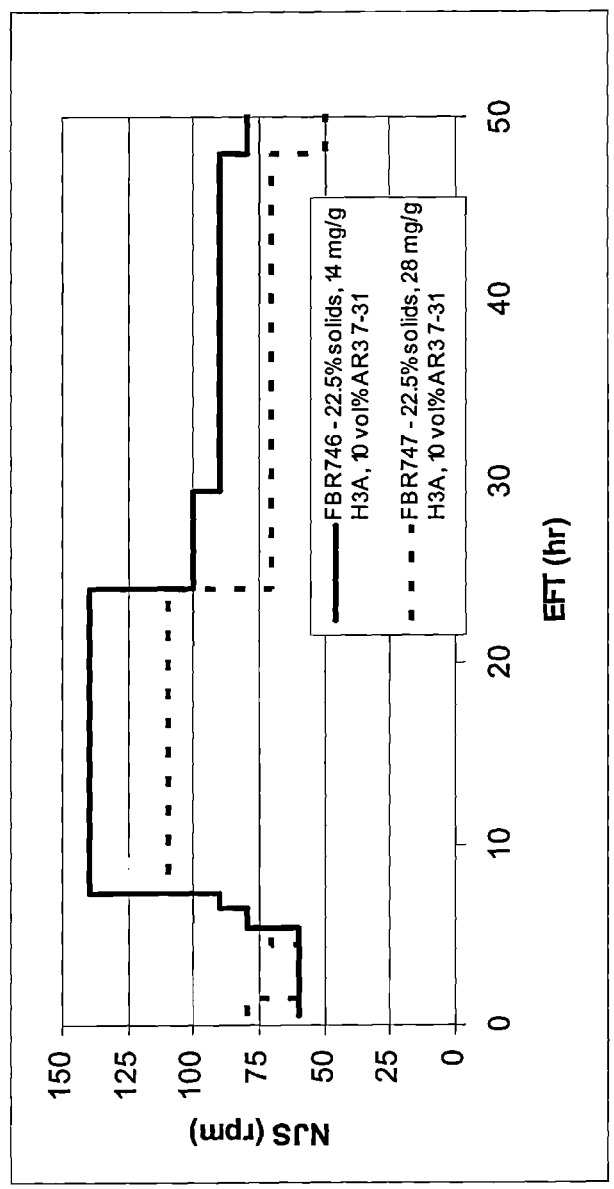
Figure 7B:
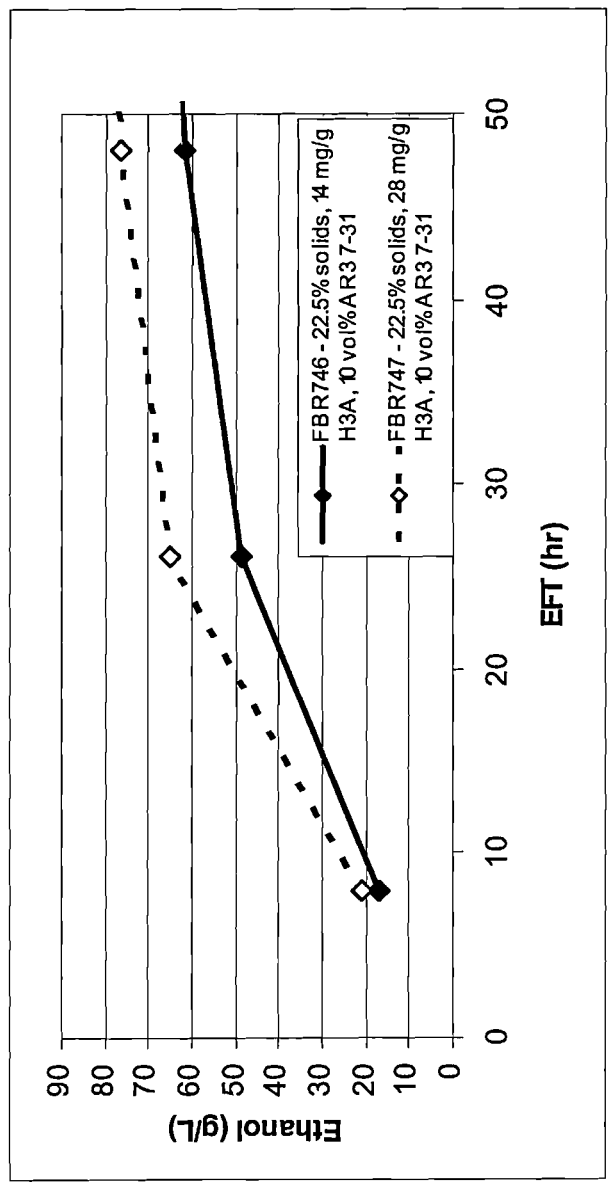

FIG. 7A is a graph of stirring rate (Njs) over time for SSF runs with 22.5% solids using strain AR3 7-31 with two different enzyme loadings. FIG. 7B is a graph of ethanol production in the same SSF runs.

Figure 8:
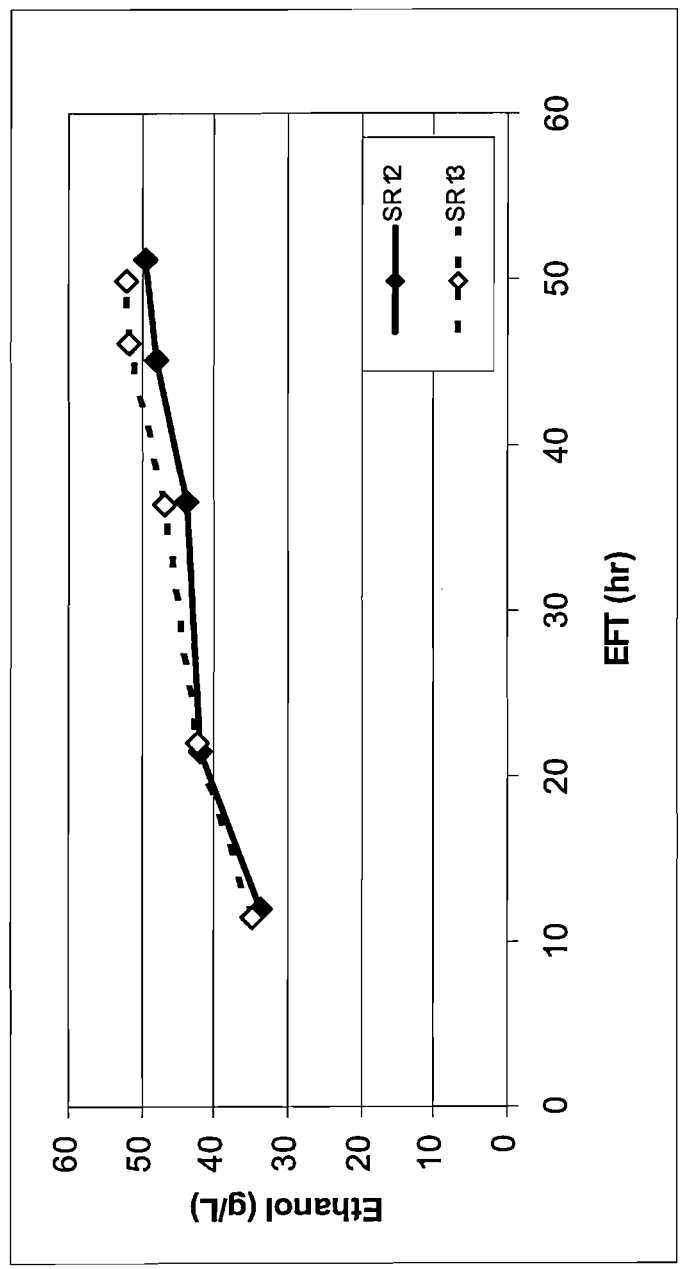

FIG. 8 shows a graph of ethanol production in SSF runs using corn stover hydrolysate and two different enzyme loadings.

Figure 9:
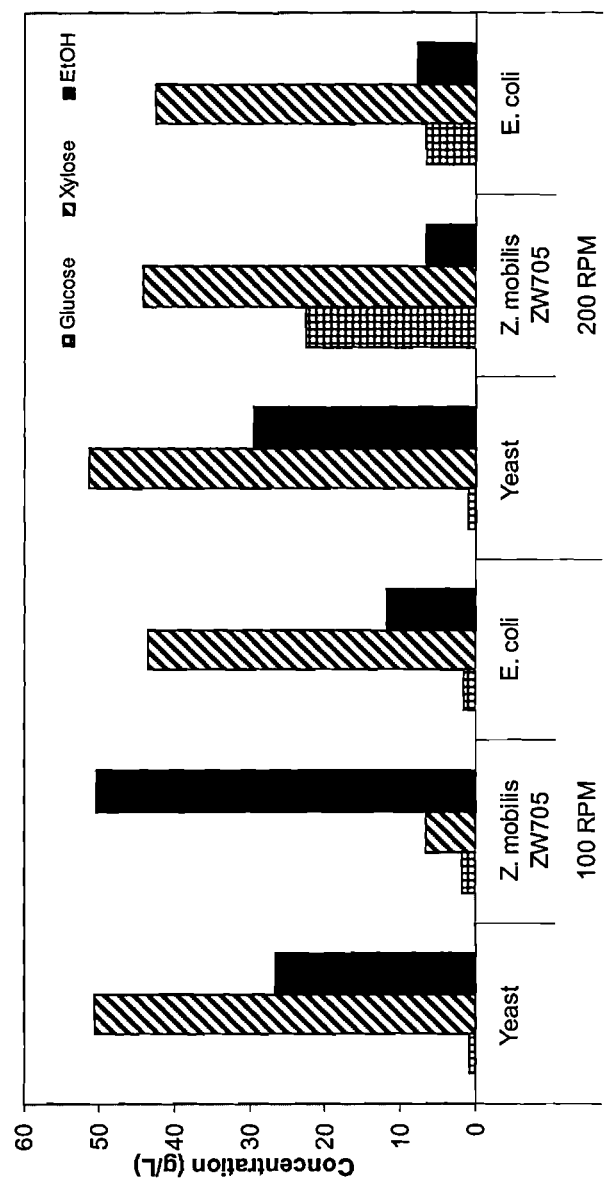

FIG. 9 shows a graph of glucose, xylose, and ethanol concentrations in SSF run samples using yeast, E. coli, or Z. mobilis as the biocatalyst.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of Fv43D, which incorporates a predicted signal sequence corresponding to positions 1 to 20.

SEQ ID NO:2 is the sequence of the immature Fv3A which incorporates a predicted signal sequence corresponding to positions 1 to 23.

SEQ ID NO:3 is the sequence of the immature Fv51A which incorporates a predicted signal sequence corresponding to positions 1 to 19.

SEQ ID NO:4 is the sequence of the immature Xyn3 which incorporates a predicted signal sequence corresponding to positions 1 to 16.

SEQ ID NO:5 is the amino acid sequence of *T. reesei* β-glucosidase Bgl1.

DETAILED DESCRIPTION OF THE INVENTION

The invention relates to the use of a prokaryotic ethanologen, such as *Zymomonas*, in a simultaneous saccharification and fermentation (SSF) process, or a hybrid saccharification and fermentation (HSF) process, for the production of ethanol from cellulosic biomass. The production of ethanol from renewable resources for use as a fuel additive will address shortages in fossil fuels, reduce energy costs and impact global warming. SSF or HSF processes are preferred in the generation of ethanol as they increase the overall efficiency of the conversion of raw cellulosic biomass to ethanol.

The following definitions and abbreviations are to be used for the interpretation of the claims and the specification.

Unless otherwise noted, all U.S. Patents and U.S. Patent Applications referenced herein are incorporated by reference in their entirety. Further, when an amount, concentration, or other value or parameter is given as a range, a preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "invention" or "present invention" as used herein is a non-limiting term and is not intended to refer to any single embodiment of the particular invention but encompasses all possible embodiments as described in the specification and the claims.

The term "ethanologen" refers to an organism that produces ethanol through metabolism of carbohydrate sources.

The term "simultaneous saccharification and fermentation (SSF)" refers to a process wherein biomass is saccharified and the fermentable sugars produced from saccharification are used by a biocatalyst to produce a product all at the same time, typically in the same reaction vessel.

The term "hybrid saccharification and fermentation (HSF)" refers to a process wherein biomass is saccharified to a limited extent (incomplete or partial saccharification), followed by continued saccharification and fermentation occurring simultaneously.

The term "fermentable sugar(s)" refers to oligosaccharides and monosaccharides that can be used as a carbon source by a microorganism in a fermentation process.

The term "partial saccharification' refers to limited saccharification of biomass where the fermentable sugars released are less than the total of fermentable sugars that would be released if saccharification is run to completion.

The term "cellulosic" refers to a composition comprising cellulose and additional components, including hemicellulose and lignin.

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, oligosaccharides and/or monosaccharides.

Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat, wheat straw, barley straw, hay, rice straw, switchgrass, waste paper, sugar cane bagasse, sorghum, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated prior to saccharification.

The term "saccharification enzyme" refers to an enzyme that can catalyze conversion of a component of biomass to fermentable sugars. Typically the enzyme is more effective when the biomass is pretreated.

The term "insoluble solids" refers to solids that do not dissolve in solution.

The term "total input insoluble solids' refers to the total dry weight of biomass insoluble solids that is included in a saccharification-fermentation mixture. When biomass is added in multiple portions, the dry weight of the insoluble solids of each portion is added together to give the total input insoluble solids. The concentration of insoluble solids in the saccharification-fermentation mixture is referenced as % based on dry weight per liter, meaning grams dry weight per liter of total saccharification-fermentation mixture, Therefore 16% based on dry weight per liter for example, means 160 grams dry weight per liter of total saccharification-fermentation mixture.

The term "agitation means" refers to a mechanism through which power may be applied to a mixture to cause mixing of the component of the mixture. Typically there is rotation motion of a mechanism causing the mixing through an agitation means.

When a range of numerical values is provided herein, it shall be understood to encompass the end-points of the range unless specifically stated otherwise. Numerical values are to be understood to have the precision of the number of significant figures provided. For example, the number 1 shall be understood to encompass a range from 0.5 to 1.4, whereas the number 1.0 shall be understood to encompass a range from 0.95 to 1.04, including the end points of the stated ranges.

The present invention relates to methods for producing ethanol using a *Zymomonas* strain in an SSF process. The method proceeds with a cellulosic biomass that is pretreated and included at high insoluble solids concentration in a saccharification-fermentation mixture comprising the *Zymomonas* ethanologen in the presence of at least one saccharification enzyme under conditions of low agitation energy. The resulting process may produce ethanol in excess of 60 g/L.

Pretreated Biomass

The biomass of the present method may be pretreated by any process that prepares the biomass for effective release of fermentable sugars during saccharification. Pretreatments are well known in the art and include, for example, treatments with acidic or basic chemicals and/or mechanical treatment for size reduction. Pretreated biomass contains insoluble solids, polysaccharides (which typically are a part of the insoluble solids), and other components including some that are inhibitory to *Zymomonas* growth and ethanol production. It is desired that pretreated biomass used in the present method has sufficiently low levels of fermentation inhibitors to allow for maximal growth and production by a prokaryotic ethanologen such as *Zymomonas* in a saccharification-fermentation mixture containing the pretreated biomass.

For example, acetate is a component of pretreated biomass that is inhibitory to *Zymomonas*. Acetate content in pretreated biomass may be lowered by washing pretreated biomass to remove acetate and other inhibitors. Alternatively, a particular pretreatment may result in acetate levels that are compatible with *Zymomonas* growth and production. The use of ammonia in pretreatment may result in lower levels of inhibitors, such as acetate, in pretreated biomass. Applicants have discovered that the ammonia-treated biomass may have an acetamide to acetate molar ratio greater than about 1 and an acetyl conversion of greater than 60%, for example greater than about 65%, or greater than about 70%. Thus with the lower inhibitor concentration, filtration and washing steps are not necessary to obtain improved sugar yields, and as the costs associated with these steps negatively impact the economics of the method, filtering and washing of the biomass is preferably omitted.

Accordingly ammonia pretreated biomass is preferred for use in the present method. It is preferred to use an ammonia concentration that is less than about 12 wt. % relative to the dry weight of biomass as in a pretreatment method that is disclosed in the commonly owned U.S. Pat. No. 7,781,191.

In addition, different *Zymomonas* or other ethanologen strains may have different levels of tolerance to acetate and/or other inhibitors that are present in pretreated biomass. *Zymomonas* strains may be sensitive to acetate levels such as 4-5 g/L. In addition, *Zymomonas* strains may be prepared to have improved tolerance to acetate, for example by genetic engineering as disclosed in commonly owned and co-pending US Patent Application Publication US 2009-0203099 A1. In addition, improved tolerance to acetate may be achieved by adaptation in acetate-containing medium, as disclosed in commonly owned and co-pending U.S. patent application Ser. No. 12/641,642, published as WO 2010/075241 which is herein incorporated by reference. *Zymomonas* strains produced using the disclosed adaptation process are suitably tolerant to at least about 9-10 g/L of acetate. For maximal *Zymomonas* growth and ethanol production, there is compatibility between the level of acetate in the pretreated biomass containing sacharification-fermentation mixture and the acetate tolerance level of the *Zymomonas* strain used for ethanol production, based on the tolerance level of the *Zymomonas* strain, where tolerance refers to the ability of a strain to grow and produce ethanol similarly in a medium with the specified level of acetate as compared to in a medium with less or no acetate.

Simultaneous Saccharification and Fermentation

The present method pertains to simultaneous saccharification and fermentation (SSF). A saccharification-fermentation mixture is prepared that includes pretreated biomass, a prokaryotic ethanologen, and at least one enzyme that converts polysaccharides of pretreated biomass to fermentable sugars. Additional media components such as sugars, salts, growth enhancers, and/or an antibiotic corresponding to an antibiotic resistance gene in the ethanologen cells are not typically necessary but can be included. Components of the pretreated biomass are saccharified, or hydrolyzed, by one or more of the saccharification enzymes to release fermentable sugars such as glucose and xylose. Sugars are released over time from the pretreated biomass. The released sugars are metabolized by the ethanologen to produce ethanol as a product.

Saccharification

Saccharification enzymes are reviewed in Lynd, L. R., et al. (Microbiol. Mol. Biol. Rev., 66:506-577, 2002). At least one enzyme is used, and typically a saccharification enzyme consortium is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in *Eur. J. Biochem.*, 223:1-5, 1994; *Eur. J. Biochem.*, 232:1-6, 1995; *Eur. J. Biochem.*, 237:1-5, 1996; *Eur. J. Biochem.*, 250:1-6, 1997; and *Eur. J. Biochem.*, 264: 610-650 1999, respectively]) of the general group "hydrolases" (EC 3.). Glycosidases useful in the present method can be categorized by the biomass components that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes (or an "enzyme consortium") having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme preparation.

Saccharification enzymes may be obtained commercially, in isolated form, such as Spezyme® CP cellulase (Danisco US, Inc, Rochester, N.Y.) and Multifect® xylanase (Danisco US, Inc.). In addition, saccharification enzymes may be unpurified and provided as a type of cell extract or whole cell preparation. The enzymes may be produced using recombinant microorganisms that have been engineered to express multiple saccharifying enzymes.

One skilled in the art would know how to determine the effective amounts of enzymes to use in the present SSF method, and adjust conditions for optimal enzyme activity in the SSF. One skilled in the art would also know how to optimize the classes of enzyme activities required to obtain optimal saccharification of a given pretreated biomass under the selected conditions.

Hybrid Saccharification And Fermentation

In addition, the present method may be performed as hybrid saccharification and fermentation (HSF). In this process saccharification occurs for a period of time prior to fermentation, where partial but not complete saccharification occurs. In this process the ethanologen is added a period of time after the pretreated biomass and saccharification enzyme are combined so that some saccharification occurs in the absence of fermentation. The period of time before ethanologen is added may vary and is typically in a range of from one to a few hours so that fermentable sugars are released and already present at a desirable concentration when the ethanologen is added. HSF is exemplified in Example 4 where *Zymomonas* cells are added one hour after addition of the saccharifying enzymes.

Prokaryotic Ethanologen

The present saccharification-fermentation mixture initially includes an inoculum of seed cells from a strain of a prokaryotic ethanologen. Any prokaryotic cell that produces ethanol effectively may be used as the ethanologen. Cells used may produce ethanol naturally, be engineered to produce ethanol, or may be natural ethanol producers that are engineered for improved ethanol production. Examples of prokaryotic ethanologens include, but are not limited to, *Clostridium* (Stevenson and Weimer (2005) *Applied and Environmental Microbiology* 71:4672-4678), strains of *E. coli* that are engineered for ethanol production (U.S. Pat. No. 5,000,000), strains of *Geobacillus thermoglucosidasius* (Cripps et al. (2009) *Metabolic Engineering* 11:398-408) that are engineered for ethanol production, strains of *Klebsiella oxytoca* that are engineered for ethanol production (Ohta et al. (1991) *Applied and Environmental Microbiology* 57:2810-2815), *Zymobacter* (Yanase et al. (2007) *Appl. Environ. Mirobiol.* 73:2592-2599), and *Zymomonas*.

Preferred as a prokaryotic ethanologen is *Zymomonas*, which naturally ferments glucose to produce ethanol. *Zymomonas* strains that have been engineered for xylose utilization (U.S. Pat. Nos. 5,514,583, 5,712,133, 6,566,107, PCT patent application number WO 95/28476, Feldmann et al. (1992) *Appl Microbiol Biotechnol* 38: 354-361, Zhang et al. (1995) *Science* 267:240-243) are useful in the present method. *Zymomonas* strains that have improvements in properties related to ethanol production have been made by genetic engineering and/or adaptation. It is preferred that a *Zymomonas* strain with multiple engineered and/or adapted improvements be used in the present method to maximize ethanol production. Improvements that have been made which may be present include but are not limited to: 1) engineering and adapting for improved xylose utilization (U.S. Pat. No. 7,223,575 and commonly owned U.S. Pat. No. 7,741,119, US-2009-0246876 A1, and US-2009-0246846 A1); 2) reducing synthesis of byproducts detrimental to ethanol production (commonly owned U.S. Pat. No. 7,741,119); 3) engineering for improved acetate tolerance (commonly owned and co-pending US Patent Application Publication No: US2009-0203099 A1, and U.S. patent application Ser. No. 12/641,642 published as WO 2010/075241).

*Zymomonas* strains with improved acetate tolerance produced such as by the process disclosed in WO 2010/075241 are preferred for use in the present method. With use of these strains, pretreated biomass may be included in the present saccharification-fermentation mixture at high concentration, while maintaining a level of acetate that is not detrimental to ethanol production without extensive washing to remove acetate from the pretreated biomass.

Typically the desired *Zymomonas* strain is grown as a seed culture. A seed culture may be grown, for example, in medium consisting of: 5-20 g/L yeast extract, 2-4 g/L potassium hydrogen phosphate, 1-5 g/L magnesium sulfate heptahydrate and 100-200 g/L glucose to OD600 nm of 10 at 32° C.-33° C., pH 5.5-5.8. The seed culture is used to start the SSF by adding a volume that is equivalent to about 10% of the saccharification-fermentation mixture volume.

Insoluble Solids in SSF

To maximize ethanol production in SSF the amount of insoluble solids, which are present in pretreated biomass, are included at a high level in the saccharification-fermentation mixture. The amount of pretreated biomass insoluble solids included correlates with the amount of fermentable sugars that can be produced during SSF, which in turn correlates with the amount of ethanol that can be produced from *Zymomonas* cells by metabolizing the fermentable sugars.

The amount of insoluble solids relative to the amount of solids in a pretreated biomass preparation will vary depending on the particular pretreatment used, as well as on whether any washing step is included. Washing will solubilize solids that are not insoluble, leaving a higher percent of insoluble solids in the total solids. Some acid pretreatments may convert as much as 30% of unpretreated biomass solids to soluble solids, leaving 70% of total solids as insoluble. In contrast, with a low ammonia pretreatment the amount of solids and amount of insoluble solids may be similar in the pretreated biomass. The amount of insoluble solids relative to total solids in a pretreated biomass sample may typically be in the range of about 70% to about 99%. For example, in the low ammonia pretreated biomass used in examples herein, the insoluble solids are 90%-91% of total solids. In the present process it is the amount of total input insoluble solids from pretreated biomass that is included in the saccharification-fermentation mixture that is important for power input effects on ethanol production by the prokaryotic ethanologen. In the present method the total amount of insoluble solids that is loaded in the saccharification-fermentation mixture is at least about 160 grams dry weight per liter of total saccharification-fermentation mixture, or 16%.

To aid in mixing of the saccharification-fermentation mixture, the pretreated biomass may be added in two or more portions. With addition of an initial portion, the insoluble solids concentration may be less than 16%. Adjustment of pH and temperature is facilitated at lower insoluble solids concentration. Additional pretreated biomass may then be added such that the total input insoluble solids loading is at least about 16%. The additional biomass may be added before or after the enzyme and/or *Zymomonas* loadings. The additional biomass may be added in one or more portions. The total input insoluble solids loaded may be at least about 16%, 17%, 18%, 19%, 20%, 21%, 24%, 25%, 30%, 35%, 40%, 45%, 50%, or higher, including any integer between the listed numbers.

As the SSF run proceeds the amount of insoluble solids decreases as the pretreated biomass is saccharified by the saccharification enzymes present in the SSF. The insoluble solids may typically decrease to about half, or less, of the original amount after about 120 hours of a given SSF run.

Power of Agitation Means

The saccharification-fermentation mixture is agitated in a bioreactor using an agitation means to provide mixing of the components including the pretreated biomass, saccharification enzymes, *Zymomonas* cells, and optionally other medium components. Applicants have found that when a high amount of energy is provided in the agitation of a saccharification-fermentation mixture containing for example about 25% or more insoluble solids, ethanol production by the *Zymomonas* ethanologen is negatively impacted. Vigorous shaking (200 RPM) of a mixture having 25% insoluble solids concentration resulted in reduced ethanol production and reduced *Zymomonas* viability, while vigorous shaking of a mixture having 12% solids had no such effect.

Thus mixing is needed during SSF, yet the ethanol production capacity of the *Zymomonas* cells needs to be maintained. Applicants have calculated the power that an agitator may provide to a saccharification-fermentation mixture containing *Zymomonas* ethanologen and at least about 22.5% insoluble solids, as described in Example 5 herein, to support desired ethanol production. In the present method mixing is provided wherein the power provided by the agitation means is no more than about 0.2 watts per kilogram of total saccharification-fermentation mixture. Preferred for maximizing ethanol production is power input of less than about 0.2, 0.15, 0.1, 0.05, 0.01, 0.005, or 0.003 watts/kg of total saccharification-fermentation mixture. Agitation means may be any rotary stirrer, including any type of impeller such as a Rushton (6-blade), and any variety of pitched blade (marine, 4-blade, 3-segment). Two or more impeller blades may be used where the sum of the individual impeller powers is less than about 0.2 watt/kg. The Power may be varied over time as viscosity of the saccharification-fermentation mixture decreases due to saccharification of the biomass.

In addition, it was found that in the presence of glass beads in the size range of between 100 μm and 600 μm, the ethanol production performance of *Zymomonas* is reduced when there is vigorous stirring. Thus when biomass particle size is in this range, agitation is reduced as described above for maximal ethanol production. With biomass particle size less than about 100 μm or greater than about 600 μm, vigorous stirring may be used. However, pretreated biomass may initially be of larger particle size, but particle size reduction may occur during an SSF run. Particle size of any type of biomass may have this effect on *Zymomonas* cells, as demonstrated by the glass beads.

Conditions for SSF

The saccharification-fermentation mixture is maintained in a bioreactor with an agitation means for production of ethanol. Conditions favorable for saccharification and fermentation by *Zymomonas* are maintained. The pH is typically maintained between about 5 and about 7 using caustic solution (such as ammonium hydroxide, potassium hydroxide, or sodium hydroxide) and either sulfuric or phosphoric acid. Typically pH is maintained at 5.8 using NaOH as base and $H_2SO_4$ as acid. The temperature is maintained between about 28° C. and about 37° C. Typically temperature is maintained at about 33° C. or varied between 33° C. and 28° C. The SSF continues for at least about 40 hours, with 120 hours or more being typical for a run.

The run may be batch where minimal alterations are made such as pH adjustment, or fed-batch where components may be fed to the saccharification-fermentation mixture as the SSF proceeds. Batch and fed-batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992). In the present method components that may be added during a fed-batch run may include additional pretreated biomass and/or additional sacharification enzymes.

Concentrations of Ethanol

High ethanol production is achievable using the present method. The specific amount of ethanol produced in the present SSF method will vary depending on conditions such as the specific *Zymomonas* strain used, the type of biomass, pretreatment of the biomass, concentration of insoluble solids, and saccharifying enzymes. Typically ethanol may be produced at greater than about 40 g/L. Ethanol may be produced at, for example, about 45, about 50, about 55, about 60, about 65, about 70, about 75, about 80, or about 85 g/L.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "μL" means microliter(s), "mL" or "ml" means milliliter(s), "L" means liter(s), "nm" means nanometer(s), "mm" means millimeter(s), "cm" means centimeter(s), "μm" means micrometer(s), "mM" means millimolar, "M" means molar, "mmol" means millimole(s), "μmole" means micromole(s), "g" means gram(s), "μg" means microgram(s), "mg" means milligram(s), "kg" means kilogram(s) "g" means the gravitation constant, "RPM" or "rpm" means revolutions per minute, "h.p." means horse power, "v%" is volume %, "atm" means atmosphere, "wt %" is weight percent, "CFU" is colony forming units, "~" means approximately, "hr" means hour(s), "ρ" means density, "μ" means viscosity, "$D_I$" means impeller diameter, "RPS" means revolutions per second, "EFT" means elapsed fermentation time.

General Methods:

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Pretreatment of Cob

Corn cob was pretreated prior to enzymatic hydrolysis using the low ammonia methods described in commonly owned U.S. Pat. No. 7,781,191

A horizontal Littleford Day 130 L reactor vessel containing a jacket for passing steam around the body of the vessel was used for pretreatment to generate pretreated cob named SSL21. The vessel was loaded with cob from seed corn processing (less than 1 mm in size) to reach 46 v % reactor fill on a wet cob basis (57.5 lbs). The cob was reduced to less than 1 mm in size using a large micropulverizer (Model #1 SH, Serial #10019) with a 1.0 mm screen. A scoop of dry ice was added as needed to the cob before grinding to prevent the equipment from heating up. The main drive of the micropulverizer is a 5 h.p. motor, with a maximum rotor speed of 9,600 RPM. It has six rotating hammers; shell, and is lined with opposing impact edges.

The cob had a wet loose bulk density of 0.420 g/cm³ and 7.5 wt % moisture. Vacuum was applied to the vessel to reach 0.1 atm prior to introduction of a 28.9 wt % ammonium hydroxide solution (11.2 lbs) and water (20.1 lbs) near the top of the vessel to give a 6 wt % NH3 relative to dry weight biomass and 60 wt % solids inside the vessel. Table 1 lists cob properties and ammonium hydroxide and water amounts used for a second pretreatment batch named SSL22. In both cases, the reactor agitator was set to 70 rpm and steam was passed through the jacket of the vessel. When the vessel reached an internal temperature of 80° C. steam was introduced near the top of the vessel to raise the internal vessel temperature to 145° C. This temperature was held for 20 minutes. At 15 minutes of this hold-up time the steam flow through the jacket was stopped. At the end of pretreatment, the reactor was depressurized through a vent condenser to reach atmospheric pressure. Vacuum (approximately to less than 1 atm) was subsequently applied for 15 minutes to lower the temperature to less than 60° C. and remove additional ammonia and water from the pretreated cob prior to opening the bottom valve of the vessel and recovering the pretreated biomass. Table 2 lists the pretreated cob specifications for SSL21 and SSL22 batches. A residual ammonia of less than 0.3 kg NH3/100 kg dry solids is desired as well as an acetamide to acetic acid ratio of greater than 1.0.

Insoluble solids were determined to be 90%-91% of total solids for the SSL21 pretreated cob batch.

TABLE 1

Cob properties and ammonium hydroxide and water amounts used for a second pretreatment batch (SSL 22).

| Loose wet bulk density (g/cm$^3$) | Cob % moisture | Cob amount on wet basis (lbs) | NH$_4$OH amount (lbs) | Water amount (lbs) |
|---|---|---|---|---|
| 0.416 | 10.4 | 54.8 | 10.3 | 16.8 |

TABLE 2

Pretreated cob specifications for SSL21 and SSL22 batches

| Batch | Wt % solids final | Residual NH$_3$ at pH 5.3 (kg NH$_3$/100 kg dry solids) | Acetamide/acetic acid ratio |
|---|---|---|---|
| SSL 21 | 67.3 | 0.156 | 1.1 |
| SSL 22 | 69.1 | 0.17 | 1.2 |

Cob Composition

The amount of glucan and xylan in starting cob was determined using methods well known in the art, such as ASTM E1758-01 "Standard method for the determination of carbohydrates by HPLC" and as further detailed n National Renewable Energy Lagoratory (Golden, Colo.) Technical Report NREL/TP-510-42618 (revised April 2008). The composition was determined to be 34.8 wt. % glucan, 29.2 wt. % xylan, and 12.8 wt. % lignin based on dry weight.

Pretreatment of Stover

Corn stover was pretreated prior to enzymatic hydrolysis using low ammonia methods described in commonly owned and co-pending United States Patent Application Publication US-2007/0031918-A1.

Second pass corn stover was milled to the average d50 particle size of 2 mm. The stover had a loose bulk density of 0.183 g/cm$^3$ and 8.73 wt % moisture. About 109-117 kg of the pre-milled stover was loaded into a 1700 L horizontal cylindrical pressure vessel. Vacuum was applied to the vessel to reach 0.1 atm prior to feeding ammonium hydroxide solution and water to attain about 11% NH$_3$ with respect to dry matter. An impeller in the vessel was rotated at approximately 37 rpm and steam was passed through the jacket of the vessel throughout the run. Steam was introduced to the vessel to raise the internal vessel temperature to about 150° C. This temperature was held for 30 minutes under the constant reactor pressure of about 8 bar (abs; 0.8 megapascal). At the end of pretreatment, the reactor was depressurized through a vent condenser to reach atmospheric pressure. Vacuum (approximately to less than 1 atm) was subsequently applied for 4 to 8 minutes to lower the temperature to less than 60° C. and to remove the additional ammonia and water from the pretreated stover prior to opening the bottom valve of the vessel and recovering the pretreated biomass.

The second pass stover was not analyzed for its composition, however, the compositional components were estimated in Table 3 based on prior stover determinations.

TABLE 3

Assumed composition of second pass corn stover

| Biomass Number | Glucan | Xylan | Arabinan | Lignin | Acetyls |
|---|---|---|---|---|---|
| 2$^{nd}$ pass corn stover | 32.96% | 20.06% | 2.66% | 24.14% | 2.76% |

Cellulase and Hemicellulase Production Strain

Strain H3A is a recombinant *Trichoderma reesei* strain that was prepared as follows. A *Trichoderma reesei* mutant strain, derived from RL-P37 (Sheir-Neiss, G et al. Appl. Microbiol. Biotechnol. 1984, 20:46-53) and selected for high cellulase production was co-transformed with a β-glucosidase expression cassette (comprising a cbh1 promoter, a β-glucosidase1 coding region (SEQ ID NO:5), a cbh1 terminator, and an amdS gene), and an endoxylanase expression cassette (comprising a cbh1promoter, an endoxylanase coding region, and a cbh1 terminator) (SEQ ID NO: 4) using electroporation. One transformant was called strain #229. Strain #229 was co-transformed with a β-xylosidase Fv3A (SEQ ID INO: 2) expression cassette (comprising a cbh1 promoter, a β-xylosidase coding region, a cbh1 terminator, and an als gene), a β-xylosidase Fv43D expression cassette (comprising an eg1 promoter, a β-xylosidase coding region, (SEQ ID NO: 1) and a native terminator), and a Fv51A α-arabinofuranosidase expression cassette (comprising an eg1 promoter, an L-α-arabinofuranosidase coding region (SEQ ID NO:3), and a native terminator) using electroporation. Strain H3A was isolated from this transformation step.

The extracellular protein produced during fermentation of strain H3A were separated from the cell mass by centrifugation, concentrated by membrane-ultrafiltration through a Millipore 10 kD molecular cut off weight membrane, and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem 177:752). This H3A extracellular protein preparation, also termed herein as H3A protein, was used as a combination cellulase and hemicellulase preparation effecting complex carbohydrate hydrolysis during SSF.

Extra cellular protein produced during fermentation of strain H3A was separated from the cell mass by centrifugation, concentrated by membrane-ultrafiltration through a Millipore 10 kD molecular cut off weight membrane and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem 177:752). This H3A extracellular protein preparation, called herein H3A protein, was used as a combination cellulase and hemicellulase preparation effecting complex carbohydrate hydrolysis during SSF.

Biocatalyst and Inoculum Preparation

Origin of the *Zymomonas Mobilis* Strains Used in Simultaneous Saccarification and Fermentation (SSF)

Xylose-utilizing, ethanol producing strains of *Zymomonas mobilis* can be used in SSF. *Zymomonas mobilis* strain ZW705 was produced from strain ZW801-4 as briefly restated here. ZW801-4 is a recombinant xylose-utilizing strain of *Z. mobilis* that was described in commonly owned U.S. Pat. No. 7,741,119, which is herein incorporated by reference. Strain ZW801-4 was derived from strain ZW800, which was derived from strain ZW658, all as described in U.S. Pat. No. 7,741,119. ZW658 was constructed by integrating two operons, PgapxylAB and Pgaptaltkt, containing four xylose-utilizing genes encoding xylose isomerase, xylulokinase, transaldolase and transketolase, into the genome of ZW1 (ATCC 31821) via sequential transposition events, and followed by adaptation on selective media containing xylose. ZW658 was deposited as ATCC PTA-7858. In ZW658, the gene encoding glucose-fructose oxidoreductase was insertionally-inactivated using host-mediated, double-crossover, homologous recombination and spectinomycin resistance as a selectable marker to create ZW800. The spectinomycin resistance marker, which was bounded by loxP sites, was removed by site specific recombination using Cre recombinase to create ZW801-4.

Cultures of *Z. mobilis* strain ZW801-4 were grown under conditions of stress, as disclosed in U.S. patent application Ser. No. 12/641,642 published as WO 2010/075241, which is incorporated herein by reference, as follows. A continuous culture of ZW801-4 was run in 250 ml stirred, pH and temperature controlled fermentors (Sixfors; Bottmingen, Switzerland). The basal medium for fermentation was 5 g/L yeast extract, 15 mM ammonium phosphate, 1 g/L magnesium sulfate, 10 mM sorbitol, 50 g/L xylose and 50 g/L glucose. Adaptation to growth in the presence of high concentrations of acetate and ammonia was effected by gradually increasing the concentration of ammonium acetate added to the above continuous culture media while maintaining an established growth rate as measured by the specific dilution rate over a period of 97 days. Ammonium acetate was increased to a concentration of 160 mM. Further increases in ammonium ion concentration were achieved by addition of ammonium phosphate to a final total ammonium ion concentration of 210 mM by the end of 139 days of continuous culture. Strain ZW705 was isolated from the adapted population by plating to single colonies and amplification of one chosen colony.

*Zymomonas mobilis* strain AR3 7-31 (also called Adapted 7-31) was derived from strain ZW705 by adaptation for growth in hydrolysate medium as described in commonly owned and co-pending Attorney Docket #CL5332, which is herein incorporated by reference. Adaptation was in a turbidostat which is a continuous flow culture device where the concentration of cells in the culture was kept constant by controlling the flow of medium, such that the turbidity of the culture was kept within certain narrow limits as described in U.S. Pat. No. 6,686,194. Two media were available to the growing culture in the continuous culture device, a resting medium (Medium A) and a challenge medium (Medium B). A culture was grown on a resting medium in a growth chamber to a turbidity set point and then was diluted at a dilution rate set to maintain that cell density. Dilution was performed by adding media at a defined volume once every 10 minutes. When the turbidostat entered a media challenge mode, the choice of adding challenge medium or resting medium was made based on the rate of return to the set point after the previous media addition. The steady state concentration of media in the growth chamber was a mix of Medium A and Medium B, with the proportions of the two media dependent upon the rate of draw from each media that allowed maintenance of the set cell density at the set dilution rate. A sample of cells representative of the population in the growth chamber was recovered from the outflow of the turbostat (in a trap chamber) at weekly intervals. The cell sample was grown once in MRM3G6 media and saved as a glycerol stock at −80° C.

Cultures were grown using resting medium that was 50% HAc/YE and 50% MRM3G6.5X4.5NH$_4$Ac12.3, and challenge medium that was HAc/YE. Samples taken weekly were assayed in HAc/YE medium for glucose and xylose utilization, and ethanol production. Colonies were isolated from the week 3 sample and those with good growth on MRM3X2 and MRM3G2 plates were chosen. Strains from these colonies were screened for glucose and xylose utilization, and ethanol production in HAc/YE medium. Strain 12-18X-2-36 was chosen for an additional round of adaptation using HAc/YE as resting medium and HAc/YE+9 weight % ethanol. as the challenge medium. From a week 2 sample a strain called Adapted 7-31 (also called AR3 7-3) was chosen following screening of strains from the adaptation, for its increase utilization of glucose and xylose, and increased production of ethanol when grown in HAc/YE+9 weight % ethanol medium.

Media Used in Adaptation

HAc/YE: contains corn cob hydrolysate produced by pre-treating ground cob biomass with a low concentration ammonia followed by enzymatic saccharification. The hydrolysate was supplemented with 6.2 g/L ammonium acetate and 0.5% yeast extract.

MRM3 contains per liter: yeast extract (10 g), KH$_2$PO$_4$ (2 g) and MgSO$_4$.7H$_2$O (1 g).

MRM3G6.5X4.5NH$_4$Ac12.3: MRM3 with 65 g/L glucose, 45 g/L xylose, and 12.3 g/L ammonium acetate MRM3G6: MRM3 with 60 g/L glucose MRM3X2: MRM3 with 20 g/L xylose MRM3G2: MRM3 with 20 g/L glucose Growth of Seed Cultures for SSF

*Zymomonas mobilis* ZW705 was maintained as 20% glycerol stocks frozen at −80° C. To begin culture a 2 ml stock was thawed and used to inoculate 45 ml of media consisting of: 10 g/L yeast extract, 2 g/L potassium hydrogen phosphate, 5 g/L magnesium sulfate heptahydrate and 60 g/L glucose at pH 5.8 (MRM3G6) to OD 600 nm of 0.4. The culture was grown at 33° C. in a loosely capped 50 ml tube to about 2.5 OD at 600 nm and used to inoculate a final seed culture of 150-200 g/L glucose, 2 g/L potassium dihydrogen phosphate, 5 g/L magnesium sulfate heptahydrate and 10-20 g/L yeast extract at pH 5.5. That culture was grown at 33° C. in a pH controlled and stirred fermenter to an OD600 nm of about 10 and a remaining glucose concentration such that about 120 g/L of glucose was consumed. A volume of the 10 OD seed that is equivalent to 10% of the SSF final fermentation volume was withdrawn and used to start the SSF.

HPLC Analysis

Fermentation samples were taken at timed intervals and analyzed for EtOH, residual sugars, and other metabolic products such as acetic acid and glycerol using either a Waters HPLC system (Alliance system, Waters Corp., Milford, Mass.) or an Agilent 1100 Series LC; conditions=0.6 mL/min of 0.01 N H2SO4, injection volume=5 μL, autosampler temperature=10° C., column temperature=55° C., run time=25 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Simultaneous Saccharification and Fermentation (SSF)

Flask SSF

SSF flask runs were carried out anaerobically under suitable *Zymomonas mobilis* fermentation conditions. Unless otherwise stated, SSF experiments using dilute ammonia pretreated corn cob substrate were typically carried out at 33° C., pH 5.8, and 25% solids loading by weight. 25% solids (12.5 g dry weight) of the pretreated corn cob was loaded first into a 125 mL Erlenmeyer flask, followed by the addition of deionized water pre-mixed with the required amount of 6N sulfuric acid to titrate the substrate pH to 5.8. H3A protein, described above, was used as saccharifying enzyme and was added in an amount based on a basis of mg total H3A protein/g (cellulose+xylan) in the biomass substrate. Fermentation was commenced by the addition of 10% *Zymomonas mobilis* strain ZW705 inoculum (5 g) by weight into the reaction mixture with no additional nutrients added. The anaerobic environment and $CO_2$ outgassing were maintained by a 23 Gauge needle protruding from a rubber stopper that was used to cap the flask. At the start of fermentation, all SSF runs had an initial 50 g total reaction weight in a flask and the reaction mixture consisted of pretreated corn cob, water, sulfuric acid, enzyme, and ZW705 cells. The flasks were agitated inside a shaker incubator (New Brunswick Scientific, Innova 44, Edison, N.J.) at 50 or 200 RPM with the temperature cascaded down to 30° C. from 33° C. at day 1 and to 28° C. at day 2.

SSF Scale Up—Stirred Tank Reactor

A 3 liter dished-bottom glass reactor (Applikon Biotechnology Z61101 C006, Foster City, Calif.) was used instead of the 125 mL flask. SSF was carried out at a 1000 g total reaction weight in the reactor for 144 hours. 25% (250 g) solids loading by weight was used for the scale-up studies. Approximately 75% of the dry solids were added to sterile MilliQ water and pH adjusted with 2N sulfuric acid to pH 5.8. This initial mixture was raised to and held constant at 33° C. Then, enzymes (20 mg H3A protein/g (cellulose+xylan)) and *Zymomonas* inoculum were added along with the remaining dry solids. At 24 hours, the temperature was lowered to 30° C., then to 28° C. at 48 hours. The temperature of reactor was maintained by an electrically powered heating tape wrapped around the outer surface of the reactor with the mixing provided by either a Rushton or a Marine pitched blade impeller. The headspace of the reaction was swept with nitrogen to reduce *Zymomonas* exposure to oxygen and outgas was controlled with a rubber stopper punctured with a 19 Gauge needle.

Total Viable Count (TVG)

The total viable counts for SSF samples containing *Zymomonas mobilis* cells were monitored over time by measuring colony forming units (CFU). Samples were serial diluted in sterile filtered MilliQ water, then plated onto MRM3 plates (15 g agar, 50 g glucose, 10 g yeast extract, 1 g $MgSO_4 \times 7H_2O$, 2 g $KH_2PO_4$ adjusted to pH 5.5 and autoclaved at 121° C. for 15 min), and incubated anaerobically by sealing the plate with Parafilm at 33° C. for 48 hours. Dilution plates with between 10 to 1000 colonies were counted for colony forming units (CFU). If a plate count is outside the dilution range, the CFUs are reported as less than or greater than the un-countable dilution plate.

Example 1

The Effect of RPM and Solids Loading on SSF

This example demonstrates the effect of RPM and solids loading on the SSF process using dilute ammonia pretreated corn cob and recombinant *Zymomonas mobilis* strain ZW705. SSF was performed as described in General Methods for Flask SSF. The experimental runs were carried out at three different solids loadings (6%, 12%, and 25%) and two different RPM (50 RPM and 200 RPM) with H3A protein dosed at 15 mg/g glucan+xylan. Samples were taken after 3 days and assayed by HPLC as described in Materials and Methods.

Figure 1:
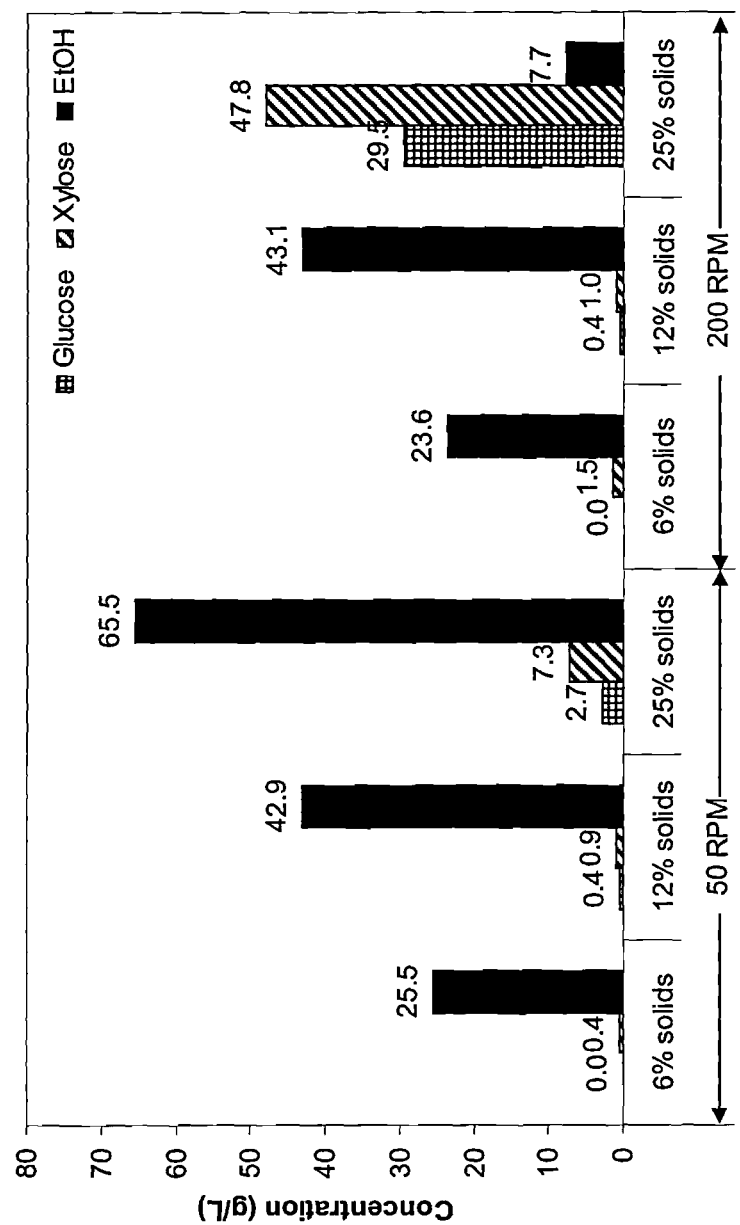
FIG. 1 is a graph showing the effects of solids loading and stirring RPM on SSF using recombinant Zymomonas and dilute ammonia pretreated corn cob with 15 mg H3A protein/g glucan+xylan.

The results given in FIG. 1 showed a surprisingly strong effect of RPM on SSF process at high solids loading (25%). The SSF with an RPM of 200 and 25% solids produced only 7.7 g/L of EtOH at day 3, which was primarily carry over ethanol from the *Zymomonas* inoculum. At the same time, 29.5 g/L of glucose and 47.8 g/L of xylose were accumulated indicating that the H3A enzyme preparation was still effective under these conditions. In contrast, at the lower solids loadings (6% and 12%), increasing RPM to 200 RPM did not result in reduced performance for the SSF process.

Figure 2:
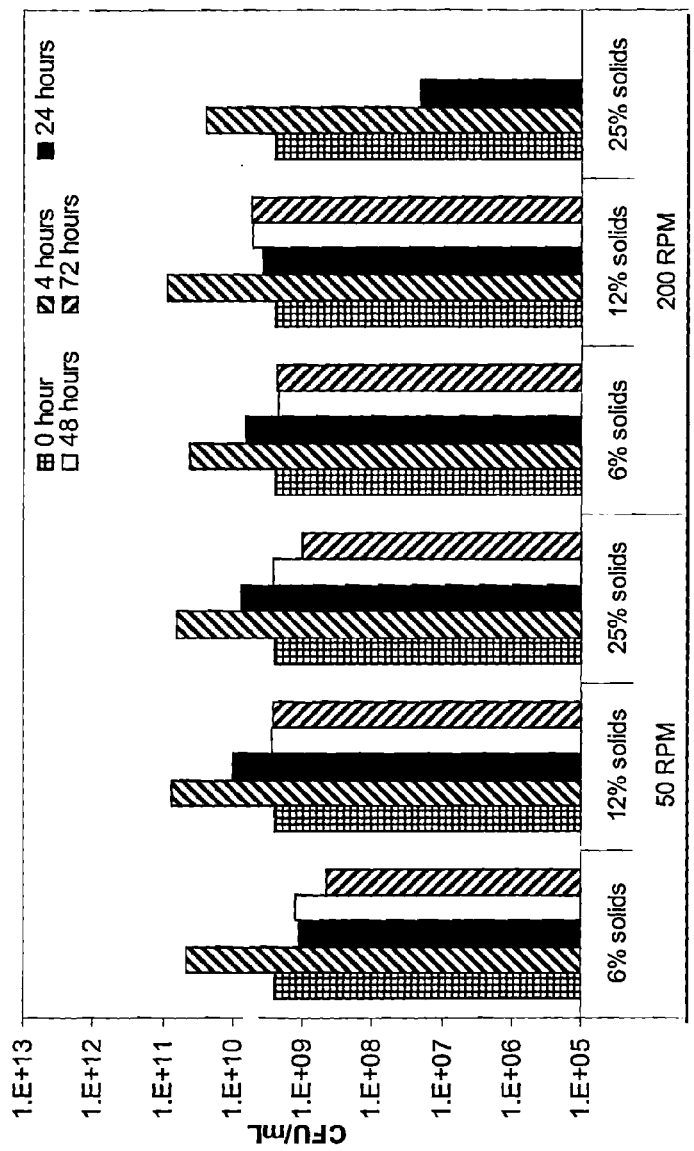
FIG. 2 is a graph showing the effect of RPM and solids loading on the viability of recombinant Zymomonas mobilis under SSF conditions using dilute ammonia pretreated corn cob with 15 mg H3A protein/g glucan+xylose.

The total viable cell counts of the above runs were monitored over time during the course of the experiment at 0, 4, 24, 48, and 72 hours as described in General Methods. The results shown in FIG. 2 indicate that the loss of SSF fermentation performance at 25% solids and 200 RPM was directly related to the loss of CFU by *Zymomonas mobilis*. For all SSF runs, the *Zymomonas* experienced a rapid growth between the inoculation (0 hour) and 4 hours. The total viable cell counts stabilized to 2 to $9 \times 10^9$ CFU/mL after 4 hours for all runs except the one at 25% solids and 200 RPM where a 3 log reduction in *Zymomonas* viability (CFU) was seen within 24 hours and a 5 log reduction was seen within 48 hours. Thus, the *Zymomonas* viability was adversely affected by the increase in the RPM, but only at high solids loadings (25%). A lower solids SSF process (6% and 12%), on the other hand, was not impacted by the increase in RPM.

Example 2

The Effect of Particle Size on Ethanol Production
High Solids Mock SSF

To study the effect of particle size on *Zymomonas* fermentation, Ballotini Soda Glass Beads (VWR, Cat#33997-500/536/560/562/568/584, West Chester, Pa.) were used in mock SSF runs instead of pretreated corn cob. Beads with the following diameter ranges were washed, sterilized and dried before use: 0-50 μm, 100-200 μm, 400-600 μm, 1250-1550 μm (1.25-1.55 mm), and 2850-3300 μm (2.85-3.30 mm). Similar to conditions described in Flask SSF, reaction size was fixed at 50 g and 25% total solids (glass beads) in stoppered 125 mL Erlenmeyer flasks with 21 Gauge needles for outgassing. In order to mimic available carbohydrates in a standard SSF reaction, media consisting of 80 g/L glucose and 70 g/L xylose was prepared in water and loaded. The media was sterilized by autoclaving at 121° C. for 15 minutes. *Zymomonas* inoculum was loaded into the reaction mixture at 10% by weight, and no enzyme was added in this case. Each reaction was carried out in a shake incubator agitated at 100 or 200 RPM with temperature maintained constant at 33° C.

The ethanol production results shown in FIG. 3A clearly indicate a performance loss when *Zymomonas* fermentation was carried out in the presence 25% solids with particle sizes of either 100-200 μm or 400-600 μm and at high RPM (200 RPM). No measurable performance reduction was seen with any other tested particle size range at 200 RPM, and with any particle size range at 100 RPM. A similar effect was seen from the CFU data as well where a 2 log decrease in CFU was seen for the 100-200 μm and 400-600 μm beads run at 200 RPM. The data in Table 4 indicates that the loss of fermentation performance is directly a result of the loss of *Zymomonas* viability.

TABLE 4

CFU determined for runs of FIG. 3.

| Ballotini beads | RPM | CFU/mL at 0 hr | CFU/mL at 24 hr |
|---|---|---|---|
| 0-50 μm | 100 | $3.5 \times 10^{10}$ | $1.9 \times 10^{9}$ |
| 100-200 μm | 100 | $3.5 \times 10^{10}$ | $8.0 \times 10^{8}$ |
| 400-600 μm | 100 | $3.5 \times 10^{10}$ | $1.7 \times 10^{9}$ |
| 1250-1550 μm | 100 | $3.5 \times 10^{10}$ | $1.2 \times 10^{9}$ |
| 2850-3300 μm | 100 | $3.5 \times 10^{10}$ | $2.8 \times 10^{9}$ |
| 0-50 μm | 200 | $3.5 \times 10^{10}$ | $1.2 \times 10^{10}$ |
| 100-200 μm | 200 | $3.5 \times 10^{10}$ | $<1.0 \times 10^{8}$ |
| 400-600 μm | 200 | $3.5 \times 10^{10}$ | $<1.0 \times 10^{8}$ |
| 1250-1550 μm | 200 | $3.5 \times 10^{10}$ | $3.1 \times 10^{9}$ |
| 2850-3300 μm | 200 | $3.5 \times 10^{10}$ | $3.0 \times 10^{9}$ |

Figure 3B:
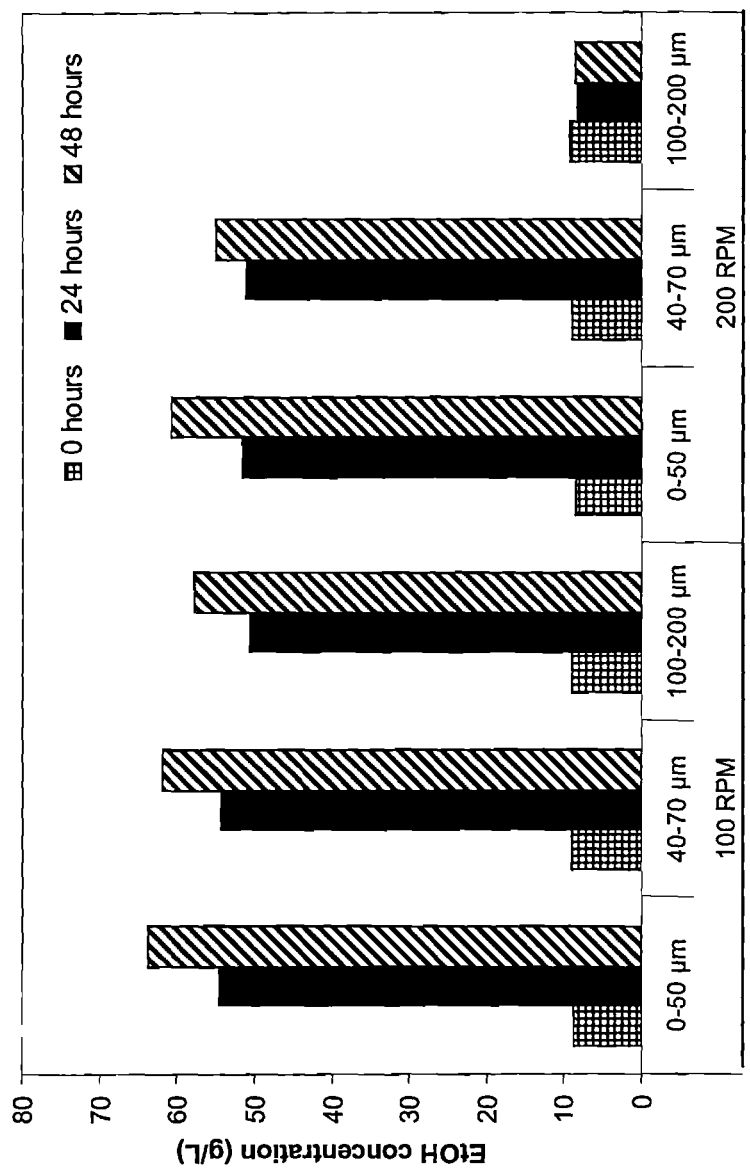

The experiment was repeated using beads with the following diameter ranges: 0-50 μm, 40-70 μm, and 100-200 μm. Results given in FIG. 3B show that ethanol production from mock SSF with 200 RPM stirring and 40-70 μm beads was similar to ethanol produced in the 100 RPM run.

The critical particle size range for reducing ethanol production and cell viability determined using Ballotini beads under conditions tested (25% solids, 50 g reaction volume in 125 mL flask, 200 RPM) was in the range between 100 μm and 600 μm.

Example 3

SSF in Stirred Tank Reactors

Trial 1

Two Rushton 6-bladed impellers (45 mm diameter) revolving at 100 RPM were used in a SSF scale up as described in Materials and Methods. Impellers were spaced 3 cm apart along the shaft with the bottom impeller spaced 2 cm from the bottom of the reactor. The Saccharifying enzyme was H3A protein which was loaded at 20 mg protein/g (glucan+xylan). With the 25% solids loading used, the Rushton impellers did not provide adequate mixing. Visual observations revealed significant solids settling, poor axial mixing, $CO_2$ build-up trapped within the reaction slurry, and highly localized radial mixing around the impellers. Due to the non homogeneous mixing, estimates of power input during the SSF run could not be made. However glucose, xylose, and ethanol concentrations were determined over 140 hours by sampling and HPLC analysis, and the pattern of glucose, xylose and ethanol accumulation (shown in FIG. 4) indicates a normal saccharification rate but incomplete fermentation. The non homogenous mixing was corrected by changing the impeller design and a second trail was run.

Trial 2

A second SSF scale up was run as above except the two Rushton impellers were replaced with two marine 6-bladed impellers (45 mm diameter). Impellers were spaced 3 cm apart along the shaft with the bottom impeller spaced 2 cm from the bottom of the reactor. Impeller speed was increased to 150 RPM. Marine impellers were known to show a reduced maximum shear rate compared to Ruston impellers (Shuler and Kargi, Bioprocess Engineering, 2nd edition, p 287 (2002) Prentice Hall, Upper Saddle River, N.J.). This may lead to poor gas dispersion and transfer in the liquid, but is of less concern since the fermentation is anaerobic. The impeller change mitigated the mixing issues previously seen in trial 1. A complete suspension of residual insoluble solids and homogenous mixing was observed visually. Glucose, xylose, and ethanol concentrations were determined over 140 hours by sampling and HPLC analysis. Results given in FIG. 5 show that the better axial mixing resulted in a faster rate of ethanol production and continued ethanol production well past 72 hours with minimized sugar accumulation. The increased rate of ethanol production indicates there is improved substrate liquefaction and saccharification as compared to trial 1. Day 6 titer for glucose, xylose and ethanol are 9.00, 12.64 and 85.88 g/L, respectively.

Example 4

Stirring Effect on SSF in a Stirred Tank Reactor

Simultaneous saccharification and fermentation (SSF) reactions were performed in a 1.7 L reactor under different mixing conditions. SSF runs were performed similarly to the stirred tank reactor SSF described in General Methods, with stirring blades described in Example 5 below, with about 1040 g total reaction weight, using pretreated corn cob as describe above with about 24% solids loading, at an enzyme loading of 14 mg H3A protein/g glucan+xylan present in the pretreated biomass, 33° C. (not reduced), and pH 5.8, with Z. mobilis ZW705 as the fermenting organism. The headspace was not swept with nitrogen.

Two reactions were performed with stirring at 250 or 750 rpm, with pretreated solids added to water to 26 weight percent. Pretreated cob preparation SSL21 was used. Each mixture was stirred to insure homogeneity while temperature and pH were adjusted. Once pH and temperature reached the desired values, the full dose of enzyme was added. One hour after the enzyme was added, the mixing was set to the desired value, and 10% (final volume) of harvest-ready Z. mobilis ZW705 seed culture, as described in General Methods, was added, bringing the final solids content to 23.6 weight percent.

Two reactions were performed with stirring at 250 or 80 rpm, with SSL22 pretreated solids added in three batches as follows.

1) Started with 554 g water+217 g pretreated biomass (69.1% dry solids)+21.81 mL (~21.81 g) enzyme=792.8 g reaction mixture with 149.9 g dry solids. Resulted in 18.9% solids (based on the reaction mixture mass at this point) or 14.4% solids (based on the final reaction mixture mass of 1040.8 g).

Once pH and temperature reached the desired values, the full dose of enzyme was added.

2) Five minutes after the enzyme was added, the mixing was set to the desired value, and 10% (final volume) of harvest-ready Z. mobilis ZW705 seed culture was added.

Added 104 ml of harvest ready Zymomonas seed culture (~104 g), so there was 896.8 g reaction mixture, still with 149.9 g dry solids. Resulted in 16.7% solids (based on reaction mixture mass at this point) or 14.4% solids (based on final reaction mixture mass=1040.8 g).

3) One hour after the enzyme was added, another batch of solids was added.

Added a 72 g (69.1% dry matter) second batch of solids=968.8 g reaction mixture with 199.7 g dry solids. Resulted in 20.6% solids (based on reaction mixture mass at this point) or 19.2% solids (based on final reaction mixture mass=1040.8 g).

4) Two hours after the enzyme was added, a final batch of solids was added.

Added a 72 g (69.1%) dry matter final batch of solids=1040.8 g reaction mixture (249.5 g dry solids). Resulted in 24.0% solids (based on reaction mixture mass at this point)= 24.0% solids (based on final reaction mixture mass=1040.8 g).

Figure 6A:
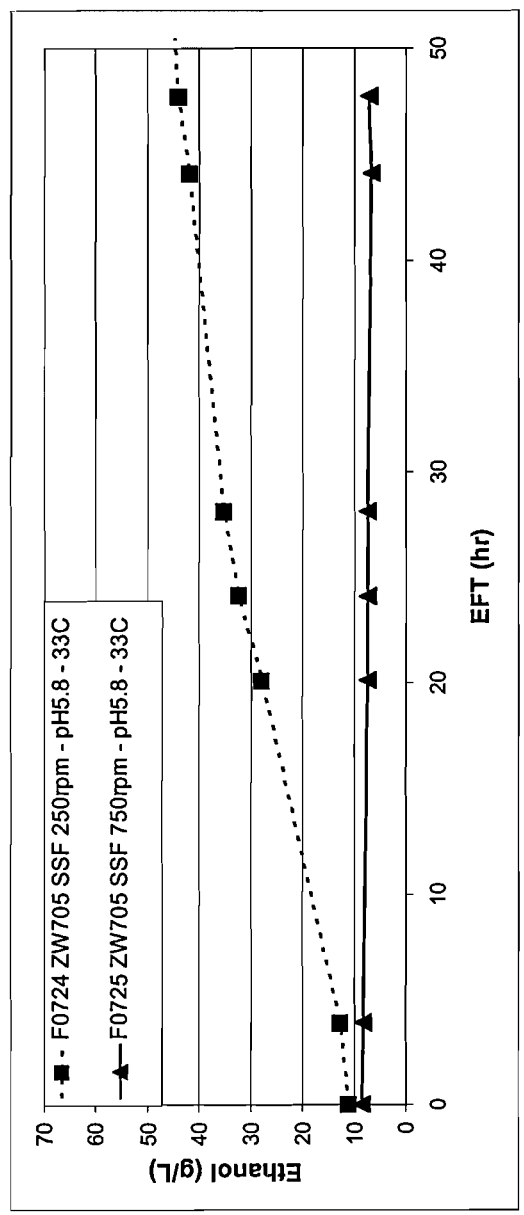
Figure 6B:
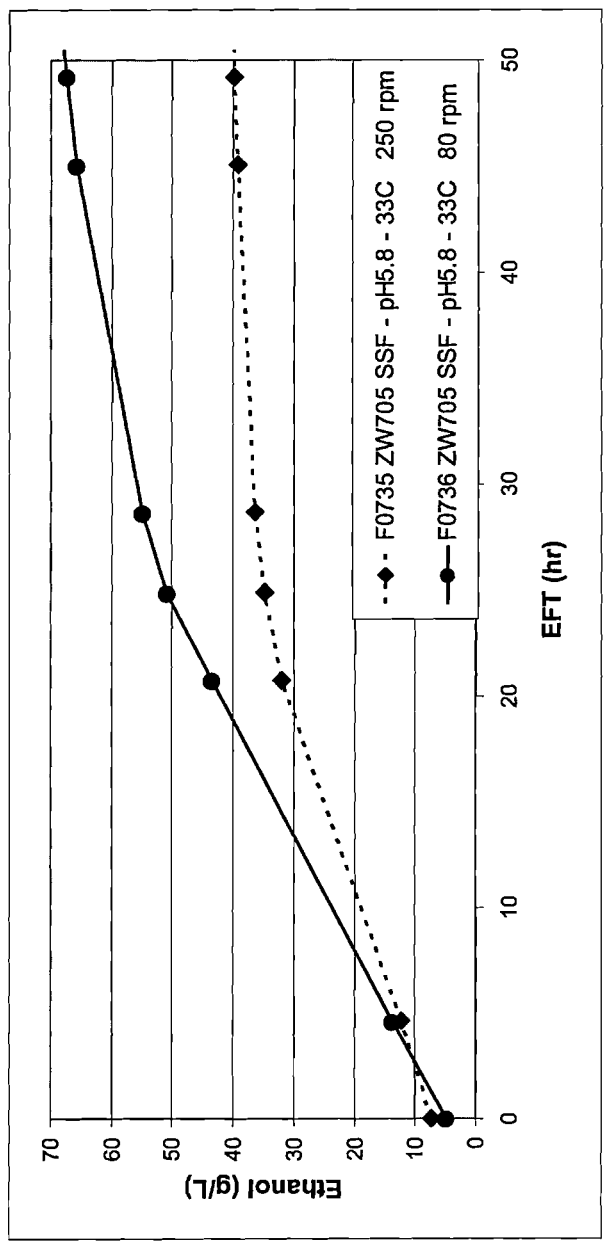

At various times, aliquots were removed from each reaction for HPLC analysis of the fermentation broth. FIG. 6A shows ethanol concentration over time for the 250 rpm and 750 rpm runs with initial 25 weight percent of solids. FIG. 6B shows the ethanol concentration over time for the 80 rpm and 250 rpm runs with partitioned addition of solids. At 750 rpm, no ethanol was produced beyond what was carried over with the seed culture (FIG. 6A). At 250 rpm, ~40 g/L ethanol was produced in ~50 hr (FIG. 6A). At 80 rpm with partitioned biomass addition, ~65 g/L ethanol was produced in ~50 hr (FIG. 6B). At 250 RPM with partitioned biomass addition, ~40 g/L ethanol was produced in ~50 hr (FIG. 6B).

Example 5

Calculation of Power Input Effect on SSF

The glass reaction vessel used in Example 4 measured 11 cm in diameter and 18 cm in height, with a dished bottom. Filling the vessel to ~1 L resulted in a working height of ~10.5 cm, producing an h/d of 0.96. Mixing was provided through agitation with a two impeller system operating at the rpm values presented above. The bottom impeller was a 3-segment impeller with a 4.8 cm diameter (B Braun Biotech) located at a liquid volume of ~350 mL (~3.7 cm off the bottom) with the segments positioned at an up-pumping 45 degree angle. The top impeller was a 6-blade turbine impeller (Rushton) with a 4.5 cm blade diameter and 2.5 cm disc, located at a liquid volume of ~700 mL (~7.4 cm off the bottom). For mixing calculations, density ($\rho$) was assumed to be 1050 kg/m3 and viscosity ($\mu$) was assumed to be that of water at 33° C. (0.00075 kg/ms). Impeller Reynolds number (Re) was calculated as $RPS*DI^2*\rho/\mu$, where RPS is revolutions per second and DI is the impeller diameter. In all cases the impeller Reynolds number was over 4000, therefore impeller power numbers were taken as the 'high Reynolds asymptote' values (1.5 for 3-segment impeller, 5 for Rushton impeller). As the impellers are well-spaced, total impeller mixing power was taken as the sum of the individual impeller mixing powers. Impeller power was calculated as the impeller power number*density*$(RPS3)*(DI^5)$. Power/mass (P/m) was obtained by dividing total impeller power by total reaction mass. Power/mass at the tip was calculated as total impeller power/$(DI^3*\rho)$. Eddy size was calculated as $[(\mu/\rho)^3/(power/mass)]^{1/4}$. For the 80, 250, and 750 rpm runs of Example 4, total impeller mixing powers were 0.0032, 0.099, and 2.7 W (power/mass of 0.0032, 0.099, and 2.7 W/kg), respectively. Impeller tip speeds in these three cases were 0.19, 0.59, and 1.8 m/s, respectively. Eddy sizes in these three cases were 104, 44, and 19 μm, respectively. Eddy size at the tip can be calculated by substituting power/mass at the tip for power/mass in the eddy size formula. Results are tabulated in Table 5.

Table 5 illustrates the strong influence of mixing on SSF success. As mixing intensity was increased, ethanol titer decreased. Under intense mixing conditions, no ethanol was formed beyond what was carried over with the seed. Specific power inputs below 0.2 W/kg of total reaction mass gave effective fermentation in SSF at high solids concentration.

Example 6

Effect of Enzyme Loading on Ethanol Titer and Stirring Requirements

Simultaneous saccharification and fermentation (SSF) reactions were performed in a 2 L reactor, with three sets of 4-bladed, 45-degree down-pumping impellers. SSF runs were performed similarly to the stirred tank reactor SSF described in General Methods, with about 2140 g total reaction weight, using pretreated corn cob as described above, with about 22.5% final solids loading, at an enzyme loading of either 14 or 28 mg H3A protein/g glucan+xylan present in the pretreated biomass, 33° C. (not reduced), and pH 5.8, with Z. mobilis AR3 7-31 as the fermenting organism. The headspace was not swept with nitrogen.

The solids were loaded in a fed-batch mode. Pretreated cob preparation SSL27 was used which contained 65.3% dry matter. Initially 94 g pretreated cob and 1120 g water were added to the reactor, creating a 5% solids slurry. pH and temperature were adjusted to the setpoints of 5.8 and 33° C., respectively. Then 40.2 g (for 14 mg/g) or 80.5 g (for 28 mg/g) of H3A enzyme were added (FBR746 and FBR747 runs, respectively), closely followed (within 5 min) by addition of 200 ml of Zymomonas cells. Over the following 7 hr, the remaining 637 g of pretreated cob were added, in equal increments each hour (total of 7 additions). pH was adjusted manually to maintain pH 5.8, using either 1N $H_2SO_4$ or 1N NaOH.

Between each solids addition and twice a day for the remainder of the run, the stirring rate was examined and adjusted, if necessary, in increments of 10 rpm such that the solids remained suspended, based on visual observation through the glass wall of the vessel. This stirring rate is referred to as $N_{JS}$ (JS="just suspended").

Graphs of $N_{JS}$ for the 14 mg/g enzyme load reactor and for the 28 mg/g enzyme load reactor are shown in FIG. 7A. The reactor with twice the enzyme loading required lower stirring rates to maintain suspension throughout the run. The maximum stirring rate required for the run which used 28 mg/g enzyme loading was 110 rpm, whereas the run with 14 mg/g enzyme loading required a maximum of 140 rpm. Since power scales with stirring rate to the third power ($P \sim N^3$), this corresponds to approximately twice the power to maintain suspension in the lower enzyme run as compared to the

TABLE 5

Mixing parameters and final ethanol titer for the Z. mobilis ZW705 SSF reactions in stirred reactors (Example 4).

| Vessel | RPM | P/m (W/kg) | NDI[#] (m/s) | Re (×1000) | Mix (s) | Eddy Size (um) | g/L Ethanol at 50 hr |
|---|---|---|---|---|---|---|---|
| 1.7 L Braun | 80 | 0.0032 | 0.19 | 4.3 | 18 | 104 | 65 |
| 1.7 L Braun | 250 | 0.099 | 0.59 | 13 | 5.7 | 44 | 40 |
| 1.7 L Braun | 750 | 2.7 | 1.8 | 40 | 1.9 | 19 | 10 |
| 3 L Applikon* | 150 | 0.0086 | 0.36 | 7.1 | 12 | 80 | 68 |

*Results from trial 2 of Example 3, which used 20 mg/g enzyme
[#]NDI is RPS*DI doubled enzyme run. Power input was calculated as in Example 5, giving 0.025 W/kg at 110 rpm and 0.052 W/kg at 140 rpm.

At various times, aliquots were removed from each reaction for HPLC analysis (as in General Methods) of the fermentation broth. FIG. 7B shows ethanol concentration over time for both reactors. The reactor with 28 mg/g enzyme loading reached about 77 g/L in 50 hr, whereas the reactor with 14 mg/g enzyme load reached about 62 g/L in the same amount of time.

Example 7

SSF Using Corn Stover

Simultaneous saccharification and fermentation (SSF) reactions were performed in a 1.7 L reactor as described in Examples 4 and 5. SSF carried out with corn stover was performed similarly to the stirred tank reactor SSF method described in General Methods.

Corn stover, prepared as described in the General methods, was used with about 20.6% final solids loading, at an enzyme loading of 17 mg H3A protein/g glucan+xylan (based on typical stover composition), 33° C. (not reduced), and an initial pH of 5.3, with Z. mobilis ZW705 as the fermenting organism. The headspace was not swept with nitrogen. The fermenter was equipped with a 3-segment impeller mounted at ~350 mL and a 6-blade turbine impeller (Rushton) mounted at ~700 mL, and the final reaction mass was about 810 g. The solids were loaded in a fed-batch mode. The pretreated stover preparation used contained 43.8% dry matter. Initially 95 g pretreated stover and 279.1 g water were added to the reactor, creating a 10% solids slurry. pH and temperature were adjusted to the setpoints of 5.3 and 33° C., respectively. The mixing rate was set to 250 rpm. Then 20.6 ml H3A enzyme were added, closely followed (within 20 min) by addition of 100 ml of Zymomonas cells. Additional doses of 95 g solids were added 1, 4.3, and 7 hr after the enzyme addition. pH was allowed to rise during solids addition, ultimately reaching a value of 5.8 after the final solids addition. The Power was calculated to be 0.111 W/kg.

At various times, aliquots were removed from the reaction for HPLC analysis of the fermentation broth. Ethanol concentration which reached 40 g/L at 27.4 hr and 45.7 g/L ethanol at 44.7 hr, further demonstrating succesful use of corn stover in SSF using about 0.1 W/kg mixing power.

Example 8

SSF with Corn Stover and Effect of Enzyme Loading

Simultaneous saccharification and fermentation (SSF) reactions were performed in a 1 L reactor. Two SSF trials with corn stover were performed similarly to the stirred tank reactor SSF described in the General Methods.

In experiment SR-12, corn stover prepared as described in the General Methods containing 43.7% dry matter was used. Solids were loaded gradually, in a fed-batch mode, with about 23.3% final solids loading in an 830 g reaction mass, at an enzyme loading of 14 mg H3A protein/g glucan+xylan in the biomass, 33° C. (not reduced), and an initial pH of 5.5, with Z. mobilis ZW705 as the fermenting organism. The headspace was not swept with nitrogen. The fermenter was equipped with 2 sets of impellers; a flat-blade turbine at approximately 14% of final reactor fill height and a 45-degree pitched-blade turbine at approximately 42% of final reactor fill height. Initially 53.0 g pretreated stover and 250 g water were added to the reactor, creating a 7.6% solids slurry. pH and temperature were adjusted to the setpoints of 5.5 and 33° C., respectively. The stirring or mixing rate was set to 168 rpm. Then 15.2 mL of H3A enzyme were added, followed by addition of 78 ml of Zymomonas cells approximately 40 min later. Additional doses of 37.0 g solids were added in ten equal additions over the next 36 hours, along with 1N $H_2SO_4$ and 1N NaOH, as needed to maintain the desired pH. For the first ~20 hours, pH was controlled (by periodic monitoring and manual adjustments) at 5.5; after 20 hours pH was controlled to 5.8 during subsequent solids additions and for the remainder of the run. The stirring rate was maintained at 168 rpm for the first 12 hours, then raised to 212 rpm until approximately 50 hours. The power input during the first 12 hours was 0.042-0.057 W/kg; variations were due to increasing reaction due to solids additions. The power input for the remainder of the run was 0.064-0.084 W/kg, again varying due to additions of mass to the reactor.

Experiment SR-13 was run identically to SR-12, however only 243 g water and 30.5 ml of enzyme were used. This represents twice the enzyme loading of the previous run, or 28 mg protein/g glucan+xylan. pH adjustments, solids additions and stirring were handled by the same methods and with the same approximate timing as the previous experiment, described above.

At various times, aliquots were removed from each reaction for HPLC analysis of the fermentation broth. FIG. 8 shows ethanol concentration over time for both runs. Experiment SR-12 reached 49.5 g/L ethanol in 51.2 hr, while experiment SR-13 reached 52.3 g/L ethanol at 50.0 hr, demonstrating that higher ethanol titers and faster rates can be achieved with higher enzyme loading in corn stover SSF.

Example 9

Comparison of RPM Effect During SSF on
Zymomonas Mobilis, Escherichia Coli, and
Saccharomyces Cerevisiae This example demonstrates the effect of RPM and solids loading on the SSF process using dilute ammonia pretreated corn cob and a variety of ethanologens, including recombinant Zymomonas mobilis strain ZW705, Escherichia coli (OneShot®TOP10 chemically competent cells, Invitrogen), and a commercial Saccharomyces cerevisiae (Ethanol Red®; Fermentis, Lesaffre Group). SSF was performed as described in General Methods for Flask SSF. S. cerevisiae starter culture was prepared by adding dried Ethanol Red® to a 20 g/L glucose solution and incubating at 30° C. for 1 hr. No starter culture was prepared for E. coli, rather 1 ml of OneShot®TOP10 chemically competent cells was thawed and added directly to the SSF reaction. The experimental runs were carried out at one solids loading (25%) and two different RPM (100 RPM and 200 RPM) with H3A protein dosed at 14 mg/g glucan+xylan. Samples were taken after 3 days and assayed by HPLC as described in Materials and Methods.

The results given in FIG. 9 showed the effect of RPM on ethanol titer at 48 hr during SSF with different microorganisms. As also shown in Example 1 FIG. 1, ethanol titer during SSF with Z. mobils ZW705 was sensitive to mixing, with the 100 RPM run resulting in an ethanol titer over 50 g/L, while the 200 RPM run did not reach 10 g/L. E. coli was also sensitive to mixing, though not to the same degree as Z. mobilis, producing 50% more ethanol at 100 RPM vs. 200 RPM (11.8 vs. 7.7 g/L, respectively) and leaving less residual glucose. S. cerevisiae, in both mixing runs, produced between 25 and 30 g/L ethanol, with slightly higher titer in the 200 rpm run. Thus, the prokaryotic ethanologens tested were adversely affected by the increase in the RPM, while the fungal ethanologen was not.

What is claimed is:

1. A method for the production of ethanol comprising:
   a) providing pretreated biomass comprising insoluble solids and polysaccharides;
   b) providing at least one saccharification enzyme for the conversion of polysaccharides to fermentable sugars;
   c) providing a prokaryotic ethanologen;
   d) preparing, in a bioreactor comprising agitation using an impeller, a saccharification-fermentation mixture comprising the pretreated biomass of a), the saccharification enzyme of b), and the prokaryotic ethanologen of c); and
   e) growing the prokaryotic ethanologen in the saccharification-fermentation mixture wherein, the concentration of total input insoluble solids in the saccharification-fermentation mixture is at least about 16% based on dry weight per liter, wherein the agitation provides an impeller power to mass radio of no more than about 0.2 watt/kg of total saccharification-fermentation mixture in the presence of biomass particles of size between 100 μm and 600 μm, and wherein the prokaryotic ethanologen produces ethanol.

2. The method of claim 1 wherein the prokaryotic ethanologen is a member of a genus selected from the group consisting of *Zymomonas, Zymobacter, Clostridium, Escherichia, Klebsiella,* and *Geobacillus.*

3. The method of claim 1 wherein the agitation using a rotary stirrer comprises at least one impeller.

4. The method of claim 1 wherein the ethanologen of c) is added at a time after addition of the saccharification enzyme of b) when partial saccharification has occurred.

5. The method of claim 1 wherein pretreated biomass is added in at least two portions that in combination give a total input insoluble solids concentration of at least about 16% based on dry weight per liter.

6. The method of claim 1 wherein the concentration of total input insoluble solids in the saccharification-fermentation mixture is at least about 20% based on dry weight per liter.

7. The method of claim 1 wherein the prokaryotic ethanologen is tolerant to the acetate concentration in the saccharification-fermentation mixture.

8. The method of claim 1 wherein biomass is selected from the group consisting of switchgrass, waste paper, sludge from paper manufacture, corn cobs, corn husks, corn stover, grasses, wheat, wheat straw, hay, barley straw, rice straw, sugar cane bagasse, sorghum, components obtained from processing of grains, trees, branches, roots, leaves, wood chips, sawdust, shrubs and bushes, vegetables, fruits, flowers and animal manure.

9. The method of claim 1 wherein the pretreated biomass is produced by treating cellulosic biomass with ammonia.

10. The method of claim 9 wherein the ammonia is less than about 12 weight percent relative to dry weight of biomass.

11. The method of claim 1 wherein the at least one saccharification enzyme is selected from the group consisting of cellulose-hydrolyzing glycosidases and hemicellulose-hydrolyzing glycosidases 12. The method of claim 1 wherein the at least one saccharification enzyme is a member of an enzyme consortium.

13. The method of claim 12 wherein the saccharification enzyme consortium comprises enzymes selected from the group consisting of cellulases, endoglucanases, exoglucanases, cellobiohydrolases, β-glucosidases, xylanases, endoxylanases, exoxylanases, β-xylosidases, arabino-xylanases, mannases, galactases, pectinases, glucuronidases, amylases, α-amylases, β-amylases, glucoamylases, α-glucosidases, isoamylases, peptidases, lipases, ligninases, and feruloyl esterases.

14. The method of claim 1 wherein the polysaccharides comprise xylan and glucan.

15. The method of claim 1 wherein the fermentable sugars comprise xylose and glucose.

16. The method of claim 1 wherein the concentration of ethanol produced is at least about 40 g/L.

17. A saccharification-fermentation system comprising:
   a) a pretreated biomass comprising insoluble solids and polysaccharides;
   b) at least one saccharification enzyme for the conversion of polysaccharides to fermentable sugars; and
   c) a prokaryotic ethanologen;

wherein the biomass of a), enzyme of b), and ethanologen of (c) are combined in a saccharification-fermentation mixture, having a concentration of total input insoluble solids that is at least about 16% based on dry weight per liter in a bioreactor comprising agitation using a rotary stirrer, and wherein the agitation provides no more power than about 0.2 watt/kg of total saccharification-fermentation mixture in the presence of biomass particles of size between 100 µm and 600 µm.

18. The saccharification-fermentation system of claim 17 wherein the prokaryotic ethanologen is selected from the group consisting of *Zymomonas, Zymobacter, Clostridium, Escherichia, Klebsiella*, and *Geobacillus*.

* * * * *

SEQUENCE LISTING

<160> NUMBER OF SEQ ID NOS: 5

<210> SEQ ID NO 1
<211> LENGTH: 350
<212> TYPE: PRT
<213> ORGANISM: Fusarium verticillioides

<400> SEQUENCE: 1

```
Met Gln Leu Lys Phe Leu Ser Ser Ala Leu Leu Ser Leu Thr Gly
1               5                   10                  15

Asn Cys Ala Ala Gln Asp Thr Asn Asp Ile Pro Pro Leu Ile Thr Asp
            20                  25                  30

Leu Trp Ser Ala Asp Pro Ser Ala His Val Phe Glu Gly Lys Leu Trp
                35                  40                  45

Val Tyr Pro Ser His Asp Ile Glu Ala Asn Val Val Asn Gly Thr Gly
        50                  55                  60

Gly Ala Gln Tyr Ala Met Arg Asp Tyr His Thr Tyr Ser Met Lys Thr
65                  70                  75                  80

Ile Tyr Gly Lys Asp Pro Val Ile Asp His Gly Val Ala Leu Ser Val
                85                  90                  95

Asp Asp Val Pro Trp Ala Lys Gln Gln Met Trp Ala Pro Asp Ala Ala
            100                 105                 110

Tyr Lys Asn Gly Lys Tyr Tyr Leu Tyr Phe Pro Ala Lys Asp Lys Asp
                115                 120                 125

Glu Ile Phe Arg Ile Gly Val Ala Val Ser Asn Lys Pro Ser Gly Pro
130                 135                 140

Phe Lys Ala Asp Lys Ser Trp Ile Pro Gly Thr Tyr Ser Ile Asp Pro
145                 150                 155                 160

Ala Ser Tyr Val Asp Thr Asn Gly Glu Ala Tyr Leu Ile Trp Gly Gly
                165                 170                 175

Ile Trp Gly Gly Gln Leu Gln Ala Trp Gln Asp His Lys Thr Phe Asn
            180                 185                 190

Glu Ser Trp Leu Gly Asp Lys Ala Ala Pro Asn Gly Thr Asn Ala Leu
                195                 200                 205

Ser Pro Gln Ile Ala Lys Leu Ser Lys Asp Met His Lys Ile Thr Glu
        210                 215                 220

Thr Pro Arg Asp Leu Val Ile Leu Ala Pro Glu Thr Gly Lys Pro Leu
225                 230                 235                 240

Gln Ala Glu Asp Asn Lys Arg Arg Phe Phe Glu Gly Pro Trp Val His
            245                 250                 255

Lys Arg Gly Lys Leu Tyr Tyr Leu Met Tyr Ser Thr Gly Asp Thr His
                260                 265                 270

Phe Leu Val Tyr Ala Thr Ser Lys Asn Ile Tyr Gly Pro Tyr Thr Tyr
            275                 280                 285

Gln Gly Lys Ile Leu Asp Pro Val Asp Gly Trp Thr Thr His Gly Ser
        290                 295                 300

Ile Val Glu Tyr Lys Gly Gln Trp Trp Leu Phe Phe Ala Asp Ala His
305                 310                 315                 320

Thr Ser Gly Lys Asp Tyr Leu Arg Gln Val Lys Ala Arg Lys Ile Trp
                325                 330                 335

Tyr Asp Lys Asp Gly Lys Ile Leu Leu Thr Arg Pro Lys Ile
            340                 345                 350
```

```
<210> SEQ ID NO 2
<211> LENGTH: 766
<212> TYPE: PRT
<213> ORGANISM: Fusarium verticilloides

<400> SEQUENCE: 2

Met Leu Leu Asn Leu Gln Val Ala Ala Ser Ala Leu Ser Leu Ser Leu
1               5                   10                  15

Leu Gly Gly Leu Ala Glu Ala Thr Pro Tyr Thr Leu Pro Asp Cys
            20                  25                  30

Thr Lys Gly Pro Leu Ser Lys Asn Gly Ile Cys Asp Thr Ser Leu Ser
            35                  40                  45

Pro Ala Lys Arg Ala Ala Leu Val Ala Ala Leu Thr Pro Glu Glu
    50                  55                  60

Lys Val Gly Asn Leu Val Ser Asn Ala Thr Gly Ala Pro Arg Ile Gly
65                  70                  75                  80

Leu Pro Arg Tyr Asn Trp Trp Asn Glu Ala Leu His Gly Leu Ala Gly
                85                  90                  95

Ser Pro Gly Gly Arg Phe Ala Asp Thr Pro Pro Tyr Asp Ala Ala Thr
            100                 105                 110

Ser Phe Pro Met Pro Leu Leu Met Ala Ala Phe Asp Asp Leu
            115                 120                 125

Ile His Asp Ile Gly Asn Val Val Gly Thr Glu Ala Arg Ala Phe Thr
130                 135                 140

Asn Gly Gly Trp Arg Gly Val Asp Phe Trp Thr Pro Asn Val Asn Pro
145                 150                 155                 160

Phe Lys Asp Pro Arg Trp Gly Arg Gly Ser Glu Thr Pro Gly Glu Asp
                165                 170                 175

Ala Leu His Val Ser Arg Tyr Ala Arg Tyr Ile Val Arg Gly Leu Glu
            180                 185                 190

Gly Asp Lys Glu Gln Arg Arg Ile Val Ala Thr Cys Lys His Tyr Ala
            195                 200                 205

Gly Asn Asp Phe Glu Asp Trp Gly Gly Phe Thr Arg His Asp Phe Asp
210                 215                 220

Ala Lys Ile Thr Pro Gln Asp Leu Ala Glu Tyr Tyr Val Arg Pro Phe
225                 230                 235                 240

Gln Glu Cys Thr Arg Asp Ala Lys Val Gly Ser Ile Met Cys Ala Tyr
                245                 250                 255

Asn Ala Val Asn Gly Ile Pro Ala Cys Ala Asn Ser Tyr Leu Gln Glu
            260                 265                 270

Thr Ile Leu Arg Gly His Trp Asn Trp Thr Arg Asp Asn Asn Trp Ile
            275                 280                 285

Thr Ser Asp Cys Gly Ala Met Gln Asp Ile Trp Gln Asn His Lys Tyr
290                 295                 300

Val Lys Thr Asn Ala Glu Gly Ala Gln Val Ala Phe Glu Asn Gly Met
305                 310                 315                 320

Asp Ser Ser Cys Glu Tyr Thr Thr Ser Asp Val Ser Asp Ser Tyr
                325                 330                 335

Lys Gln Gly Leu Leu Thr Glu Lys Leu Met Asp Arg Ser Leu Lys Arg
            340                 345                 350

Leu Phe Glu Gly Leu Val His Thr Gly Phe Phe Asp Gly Ala Lys Ala
            355                 360                 365

Gln Trp Asn Ser Leu Ser Phe Ala Asp Val Asn Thr Lys Glu Ala Gln
370                 375                 380
```

Asp Leu Ala Leu Arg Ser Ala Val Glu Gly Ala Val Leu Leu Lys Asn
385                 390                 395                 400

Asp Gly Thr Leu Pro Leu Lys Leu Lys Lys Asp Ser Val Ala Met
            405                 410                 415

Ile Gly Phe Trp Ala Asn Asp Thr Ser Lys Leu Gln Gly Gly Tyr Ser
            420                 425                 430

Gly Arg Ala Pro Phe Leu His Ser Pro Leu Tyr Ala Ala Glu Lys Leu
        435                 440                 445

Gly Leu Asp Thr Asn Val Ala Trp Gly Pro Thr Leu Gln Asn Ser Ser
    450                 455                 460

Ser His Asp Asn Trp Thr Thr Asn Ala Val Ala Ala Lys Lys Ser
465                 470                 475                 480

Asp Tyr Ile Leu Tyr Phe Gly Gly Leu Asp Ala Ser Ala Ala Gly Glu
                485                 490                 495

Asp Arg Asp Arg Glu Asn Leu Asp Trp Pro Glu Ser Gln Leu Thr Leu
            500                 505                 510

Leu Gln Lys Leu Ser Ser Leu Gly Lys Pro Leu Val Ile Gln Leu
        515                 520                 525

Gly Asp Gln Val Asp Asp Thr Ala Leu Leu Lys Asn Lys Lys Ile Asn
530                 535                 540

Ser Ile Leu Trp Val Asn Tyr Pro Gly Gln Asp Gly Gly Thr Ala Val
545                 550                 555                 560

Met Asp Leu Leu Thr Gly Arg Lys Ser Pro Ala Gly Arg Leu Pro Val
                565                 570                 575

Thr Gln Tyr Pro Ser Lys Tyr Thr Glu Gln Ile Gly Met Thr Asp Met
            580                 585                 590

Asp Leu Arg Pro Thr Lys Ser Leu Pro Gly Arg Thr Tyr Arg Trp Tyr
            595                 600                 605

Ser Thr Pro Val Leu Pro Tyr Gly Phe Gly Leu His Tyr Thr Lys Phe
        610                 615                 620

Gln Ala Lys Phe Lys Ser Asn Lys Leu Thr Phe Asp Ile Gln Lys Leu
625                 630                 635                 640

Leu Lys Gly Cys Ser Ala Gln Tyr Ser Asp Thr Cys Ala Leu Pro Pro
                645                 650                 655

Ile Gln Val Ser Val Lys Asn Thr Gly Arg Ile Thr Ser Asp Phe Val
            660                 665                 670

Ser Leu Val Phe Ile Lys Ser Glu Val Gly Pro Lys Pro Tyr Pro Leu
        675                 680                 685

Lys Thr Leu Ala Ala Tyr Gly Arg Leu His Asp Val Ala Pro Ser Ser
690                 695                 700

Thr Lys Asp Ile Ser Leu Glu Trp Thr Leu Asp Asn Ile Ala Arg Arg
705                 710                 715                 720

Gly Glu Asn Gly Asp Leu Val Val Tyr Pro Gly Thr Tyr Thr Leu Leu
                725                 730                 735

Leu Asp Glu Pro Thr Gln Ala Lys Ile Gln Val Thr Leu Thr Gly Lys
            740                 745                 750

Lys Ala Ile Leu Asp Lys Trp Pro Gln Asp Pro Lys Ser Ala
        755                 760                 765

<210> SEQ ID NO 3
<211> LENGTH: 660
<212> TYPE: PRT
<213> ORGANISM: Fusarium verticillioides

<400> SEQUENCE: 3

```
Met Val Arg Phe Ser Ser Ile Leu Ala Ala Ala Cys Phe Val Ala
1               5                   10                  15

Val Glu Ser Val Asn Ile Lys Val Asp Ser Lys Gly Gly Asn Ala Thr
            20                  25                  30

Ser Gly His Gln Tyr Gly Phe Leu His Glu Asp Ile Asn Asn Ser Gly
        35                  40                  45

Asp Gly Gly Ile Tyr Ala Glu Leu Ile Arg Asn Arg Ala Phe Gln Tyr
    50                  55                  60

Ser Lys Lys Tyr Pro Val Ser Leu Ser Gly Trp Arg Pro Ile Asn Asp
65                  70                  75                  80

Ala Lys Leu Ser Leu Asn Arg Leu Asp Thr Pro Leu Ser Asp Ala Leu
                85                  90                  95

Pro Val Ser Met Asn Val Lys Pro Gly Lys Gly Lys Ala Lys Glu Ile
            100                 105                 110

Gly Phe Leu Asn Glu Gly Tyr Trp Gly Met Asp Val Lys Lys Gln Lys
        115                 120                 125

Tyr Thr Gly Ser Phe Trp Val Lys Gly Ala Tyr Lys Gly His Phe Thr
    130                 135                 140

Ala Ser Leu Arg Ser Asn Leu Thr Asp Asp Val Phe Gly Ser Val Lys
145                 150                 155                 160

Val Lys Ser Lys Ala Asn Lys Lys Gln Trp Val His Glu Phe Val
                165                 170                 175

Leu Thr Pro Asn Lys Asn Ala Pro Asn Ser Asn Asn Thr Phe Ala Ile
            180                 185                 190

Thr Tyr Asp Pro Lys Gly Ala Asp Gly Ala Leu Asp Phe Asn Leu Ile
    195                 200                 205

Ser Leu Phe Pro Pro Thr Tyr Lys Gly Arg Lys Asn Gly Leu Arg Val
210                 215                 220

Asp Leu Ala Glu Ala Leu Glu Gly Leu His Pro Ser Leu Leu Arg Phe
225                 230                 235                 240

Pro Gly Gly Asn Met Leu Glu Gly Asn Thr Asn Lys Thr Trp Trp Asp
                245                 250                 255

Trp Lys Asp Thr Leu Gly Pro Leu Arg Asn Arg Pro Gly Phe Glu Gly
            260                 265                 270

Val Trp Asn Tyr Gln Gln Thr His Gly Leu Gly Ile Leu Glu Tyr Leu
    275                 280                 285

Gln Trp Ala Glu Asp Met Asn Leu Glu Ile Ile Val Gly Val Tyr Ala
    290                 295                 300

Gly Leu Ser Leu Asp Gly Ser Val Thr Pro Lys Asp Gln Leu Gln Pro
305                 310                 315                 320

Leu Ile Asp Asp Ala Leu Asp Glu Ile Glu Phe Ile Arg Gly Pro Val
                325                 330                 335

Thr Ser Lys Trp Gly Lys Lys Arg Ala Glu Leu Gly His Pro Lys Pro
            340                 345                 350

Phe Arg Leu Ser Tyr Val Glu Val Gly Asn Glu Asp Trp Leu Ala Gly
    355                 360                 365

Tyr Pro Thr Gly Trp Asn Ser Tyr Lys Glu Tyr Arg Phe Pro Met Phe
    370                 375                 380

Leu Glu Ala Ile Lys Lys Ala His Pro Asp Leu Thr Val Ile Ser Ser
385                 390                 395                 400

Gly Ala Ser Ile Asp Pro Val Gly Lys Lys Asp Ala Gly Phe Asp Ile
                405                 410                 415
```

-continued

```
Pro Ala Pro Gly Ile Gly Asp Tyr His Pro Tyr Arg Glu Pro Asp Val
            420                 425                 430

Leu Val Glu Glu Phe Asn Leu Phe Asp Asn Asn Lys Tyr Gly His Ile
            435                 440                 445

Ile Gly Glu Val Ala Ser Thr His Pro Asn Gly Gly Thr Gly Trp Ser
            450                 455                 460

Gly Asn Leu Met Pro Tyr Pro Trp Trp Ile Ser Gly Val Gly Glu Ala
465                 470                 475                 480

Val Ala Leu Cys Gly Tyr Glu Arg Asn Ala Asp Arg Ile Pro Gly Thr
                485                 490                 495

Phe Tyr Ala Pro Ile Leu Lys Asn Glu Asn Arg Trp Gln Trp Ala Ile
            500                 505                 510

Thr Met Ile Gln Phe Ala Ala Asp Ser Ala Met Thr Thr Arg Ser Thr
            515                 520                 525

Ser Trp Tyr Val Trp Ser Leu Phe Ala Gly His Pro Met Thr His Thr
            530                 535                 540

Leu Pro Thr Thr Ala Asp Phe Asp Pro Leu Tyr Val Ala Gly Lys
545                 550                 555                 560

Asn Glu Asp Lys Gly Thr Leu Ile Trp Lys Gly Ala Ala Tyr Asn Thr
                565                 570                 575

Thr Lys Gly Ala Asp Val Pro Val Ser Leu Ser Phe Lys Gly Val Lys
            580                 585                 590

Pro Gly Ala Gln Ala Glu Leu Thr Leu Leu Thr Asn Lys Glu Lys Asp
            595                 600                 605

Pro Phe Ala Phe Asn Asp Pro His Lys Gly Asn Asn Val Val Asp Thr
            610                 615                 620

Lys Lys Thr Val Leu Lys Ala Asp Gly Lys Gly Ala Phe Asn Phe Lys
625                 630                 635                 640

Leu Pro Asn Leu Ser Val Ala Val Leu Glu Thr Leu Lys Lys Gly Lys
                645                 650                 655

Pro Tyr Ser Ser
            660

<210> SEQ ID NO 4
<211> LENGTH: 347
<212> TYPE: PRT
<213> ORGANISM: Trichoderma reesei

<400> SEQUENCE: 4

Met Lys Ala Asn Val Ile Leu Cys Leu Leu Ala Pro Leu Val Ala Ala
1               5                   10                  15

Leu Pro Thr Glu Thr Ile His Leu Asp Pro Glu Leu Ala Ala Leu Arg
            20                  25                  30

Ala Asn Leu Thr Glu Arg Thr Ala Asp Leu Trp Asp Arg Gln Ala Ser
            35                  40                  45

Gln Ser Ile Asp Gln Leu Ile Lys Arg Lys Gly Lys Leu Tyr Phe Gly
        50                  55                  60

Thr Ala Thr Asp Arg Gly Leu Leu Gln Arg Glu Lys Asn Ala Ala Ile
65                  70                  75                  80

Ile Gln Ala Asp Leu Gly Gln Val Thr Pro Glu Asn Ser Met Lys Trp
                85                  90                  95

Gln Ser Leu Glu Asn Asn Gln Gly Gln Leu Asn Trp Gly Asp Ala Asp
            100                 105                 110

Tyr Leu Val Asn Phe Ala Gln Gln Asn Gly Lys Ser Ile Arg Gly His
            115                 120                 125
```

```
Thr Leu Ile Trp His Ser Gln Leu Pro Ala Trp Val Asn Asn Ile Asn
        130                 135                 140

Asn Ala Asp Thr Leu Arg Gln Val Ile Arg Thr His Val Ser Thr Val
145                 150                 155                 160

Val Gly Arg Tyr Lys Gly Lys Ile Arg Ala Trp Asp Val Val Asn Glu
                165                 170                 175

Ile Phe Asn Glu Asp Gly Thr Leu Arg Ser Ser Val Phe Ser Arg Leu
            180                 185                 190

Leu Gly Glu Glu Phe Val Ser Ile Ala Phe Arg Ala Ala Arg Asp Ala
        195                 200                 205

Asp Pro Ser Ala Arg Leu Tyr Ile Asn Asp Tyr Asn Leu Asp Arg Ala
    210                 215                 220

Asn Tyr Gly Lys Val Asn Gly Leu Lys Thr Tyr Val Ser Lys Trp Ile
225                 230                 235                 240

Ser Gln Gly Val Pro Ile Asp Gly Ile Gly Ser Gln Ser His Leu Ser
                245                 250                 255

Gly Gly Gly Gly Ser Gly Thr Leu Gly Ala Leu Gln Gln Leu Ala Thr
            260                 265                 270

Val Pro Val Thr Glu Leu Ala Ile Thr Glu Leu Asp Ile Gln Gly Ala
        275                 280                 285

Pro Thr Thr Asp Tyr Thr Gln Val Val Gln Ala Cys Leu Ser Val Ser
    290                 295                 300

Lys Cys Val Gly Ile Thr Val Trp Gly Ile Ser Asp Lys Asp Ser Trp
305                 310                 315                 320

Arg Ala Ser Thr Asn Pro Leu Leu Phe Asp Ala Asn Phe Asn Pro Lys
                325                 330                 335

Pro Ala Tyr Asn Ser Ile Val Gly Ile Leu Gln
            340                 345

<210> SEQ ID NO 5
<211> LENGTH: 744
<212> TYPE: PRT
<213> ORGANISM: Trichoderma reesei

<400> SEQUENCE: 5

Met Arg Tyr Arg Thr Ala Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
        50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
        115                 120                 125

Gly Glu Glu Val Lys Ala Ser Gly Ile His Val Ile Leu Gly Pro Val
    130                 135                 140

Ala Gly Pro Leu Gly Lys Thr Pro Gln Gly Gly Arg Asn Trp Glu Gly
145                 150                 155                 160
```

-continued

```
Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
        195                 200                 205

Asp Arg Thr Leu His Glu Leu Tyr Thr Trp Pro Phe Ala Asp Ala Val
    210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
        355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
        435                 440                 445

Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590
```

```
Phe Asp Asp Ala Asn Ile Thr Pro Arg Tyr Glu Phe Gly Tyr Gly Leu
    595             600             605

Ser Tyr Thr Lys Phe Asn Tyr Ser Arg Leu Ser Val Leu Ser Thr Ala
    610             615             620

Lys Ser Gly Pro Ala Thr Gly Ala Val Val Pro Gly Gly Pro Ser Asp
625             630             635             640

Leu Phe Gln Asn Val Ala Thr Val Thr Val Asp Ile Ala Asn Ser Gly
            645             650             655

Gln Val Thr Gly Ala Glu Val Ala Gln Leu Tyr Ile Thr Tyr Pro Ser
            660             665             670

Ser Ala Pro Arg Thr Pro Pro Lys Gln Leu Arg Gly Phe Ala Lys Leu
        675             680             685

Asn Leu Thr Pro Gly Gln Ser Gly Thr Ala Thr Phe Asn Ile Arg Arg
        690             695             700

Arg Asp Leu Ser Tyr Trp Asp Thr Ala Ser Gln Lys Trp Val Val Pro
705             710             715             720

Ser Gly Ser Phe Gly Ile Ser Val Gly Ala Ser Ser Arg Asp Ile Arg
            725             730             735

Leu Thr Ser Thr Leu Ser Val Ala
            740
```